United States Patent [19]
Mayeaux

[11] Patent Number: 6,122,825
[45] Date of Patent: Sep. 26, 2000

[54] METHOD OF CONSTRUCTING A SAMPLER HAVING BARRIERS AND PASSAGES

[76] Inventor: Donald P. Mayeaux, 18632 Manchac Dr., Prairieville, La. 70769

[21] Appl. No.: 09/195,394

[22] Filed: Nov. 18, 1998

Related U.S. Application Data

[63] Continuation of application No. 08/701,406, Aug. 22, 1996, Pat. No. 5,841,036.

[51] Int. Cl.$^7$ ....................................................... G01N 1/28
[52] U.S. Cl. ......................................................... 29/890.12
[58] Field of Search ........................ 29/890.12; 277/300, 277/312, 316; 73/803, 863.11, 863.12, 863.21–863.25, 863.71, 863.72, 863.73, 864.83, 864.84

[56] References Cited

U.S. PATENT DOCUMENTS

| | | | |
|---|---|---|---|
| 3,831,953 | 8/1974 | Leibfritz et al. | 277/180 |
| 4,834,946 | 5/1989 | Levin | 422/101 |
| 4,957,008 | 9/1990 | Proni et al. | 73/863.73 |
| 5,367,912 | 11/1994 | Demechi | 73/863.73 |

*Primary Examiner*—Thomas P. Noland
*Attorney, Agent, or Firm*—Joseph T. Regard, Ltd plc

[57] ABSTRACT

An in-stream sample collection and conditioning system which is easier to implement and maintain, more cost effective, and more reliable than existing systems. The preferred embodiment of the present system contemplates a modular system adaptable to a variety of diverse configurations and criteria, the system having incorporated therein a base piece formed of interconnecting modular base members, the base piece having fluid passageways formed therein to provide fluid flow between the adjacent base member. Situated adjacent to each of the modular base members forming the base piece are modular conditioning components, each selected from a field of diverse conditioning types and configurations, and adapted for the contemplated use. The present invention further contemplates a unique and useful system for joining the various modular components forming the present system, in a manner which provides redundant leak resistance, flexibility in forming various conditioning requirements and adaptability to diverse existing sampling stream interfaces, as well as a new and unique method for attachment of the transport tube to the device body. Lastly, the preferred embodiment of the present invention contemplates a highly precise, low tolerance juxtaposition of the various components forming the present system, utilizing an extremely thin sheet, formed membrane/gasket member, implemented in such a manner as to provide high thermocycling characteristics as well as high pressure tolerance, coupled with a low failure/leakage rate.

23 Claims, 22 Drawing Sheets

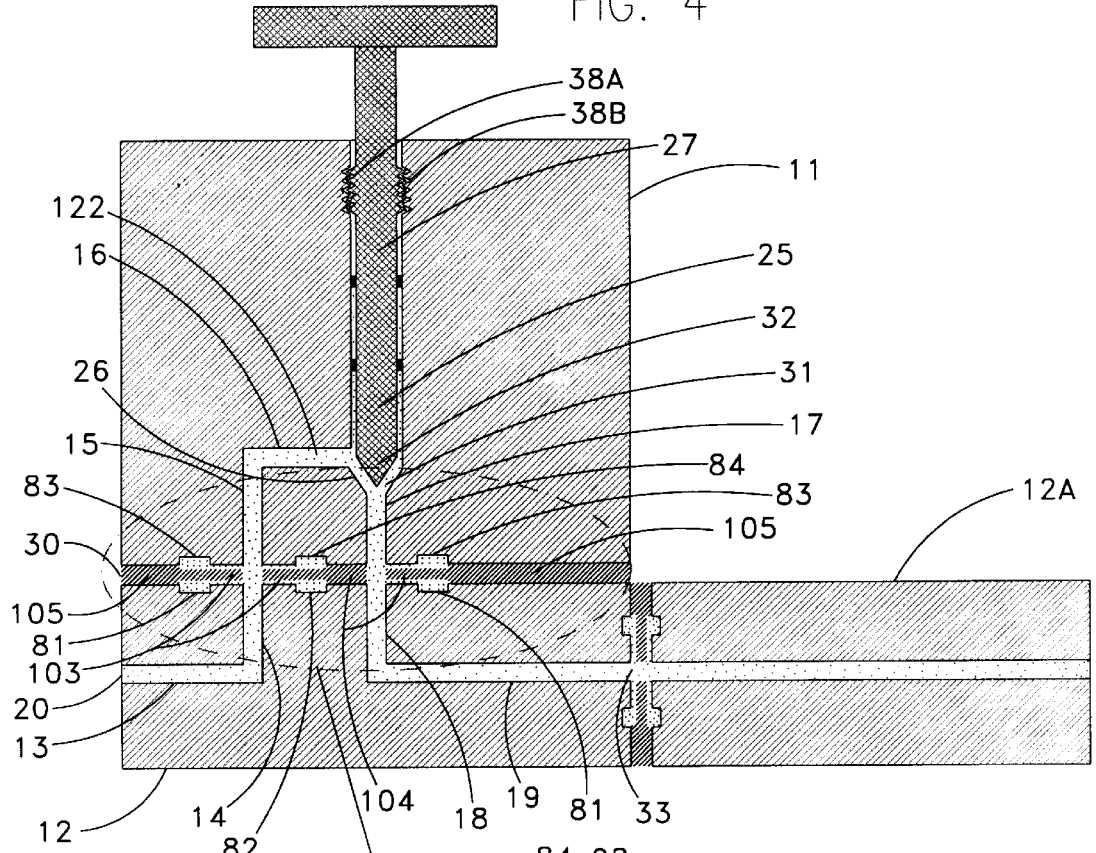
FIG. 4
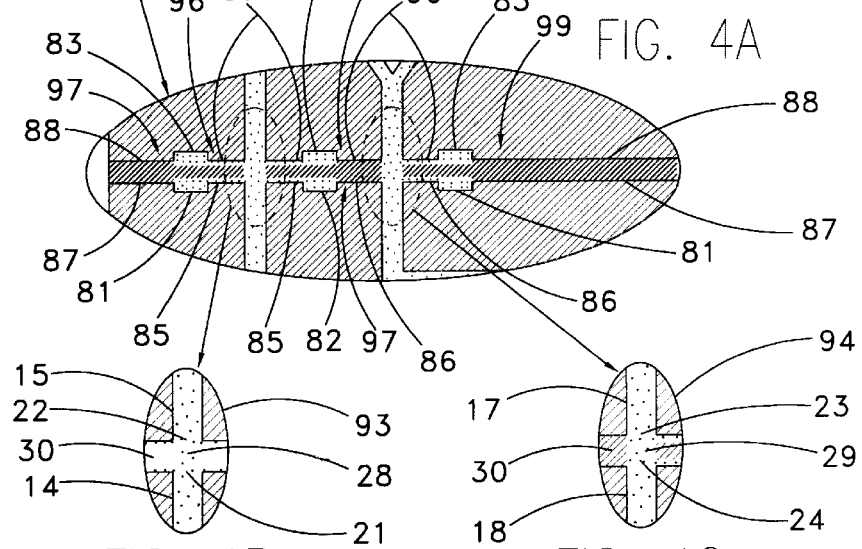
FIG. 4A
FIG. 4B
FIG. 4C

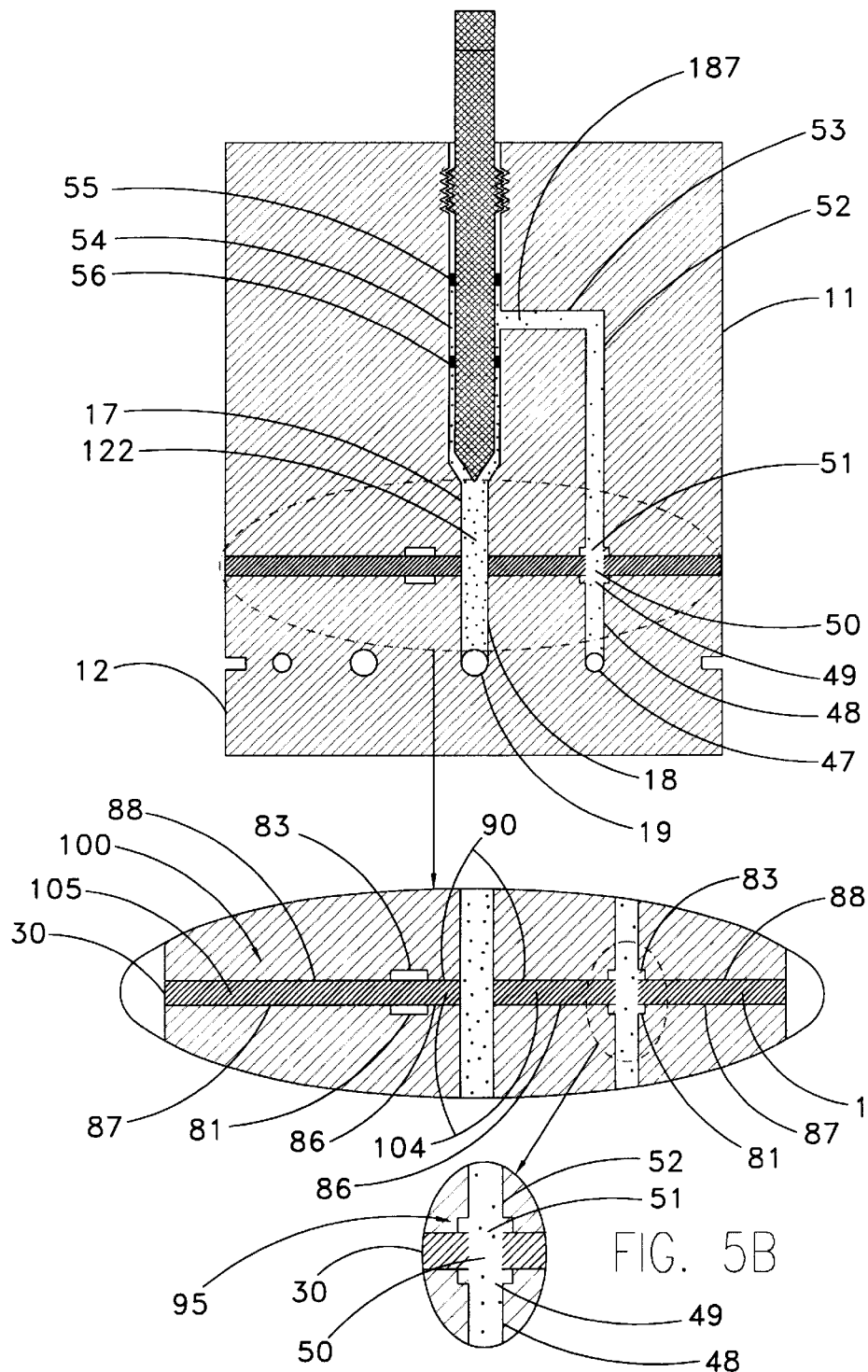

PRIOR ART

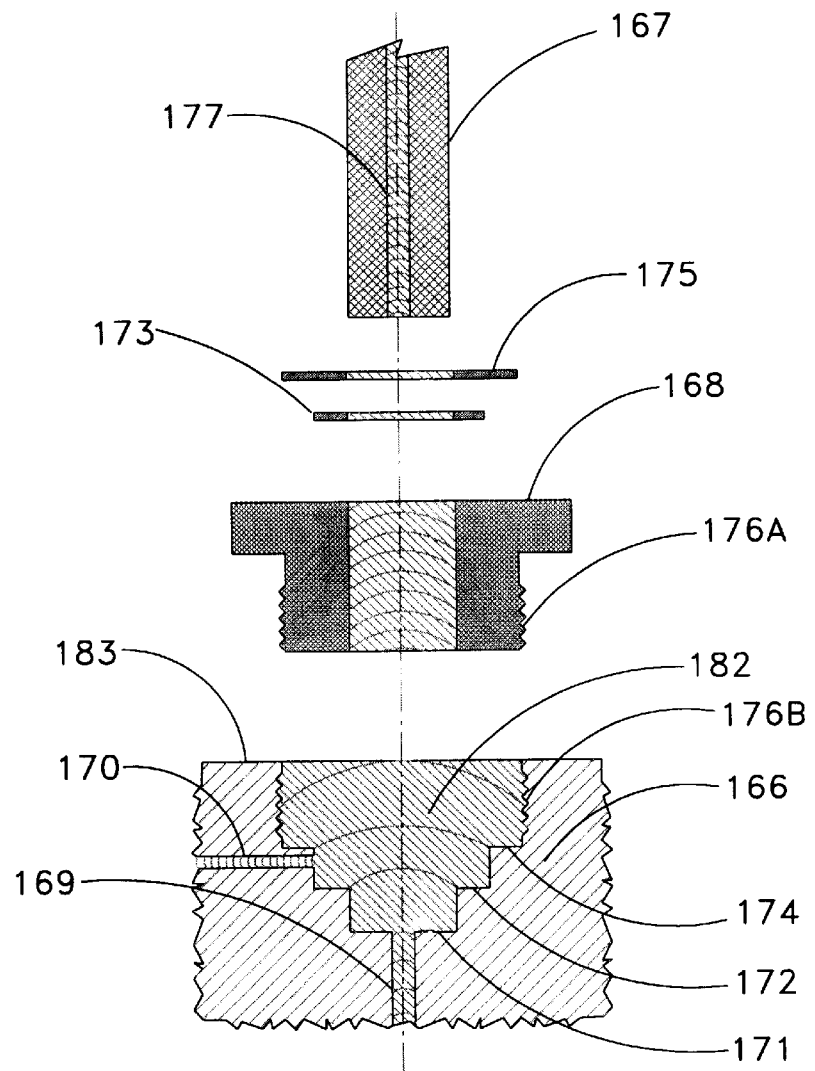
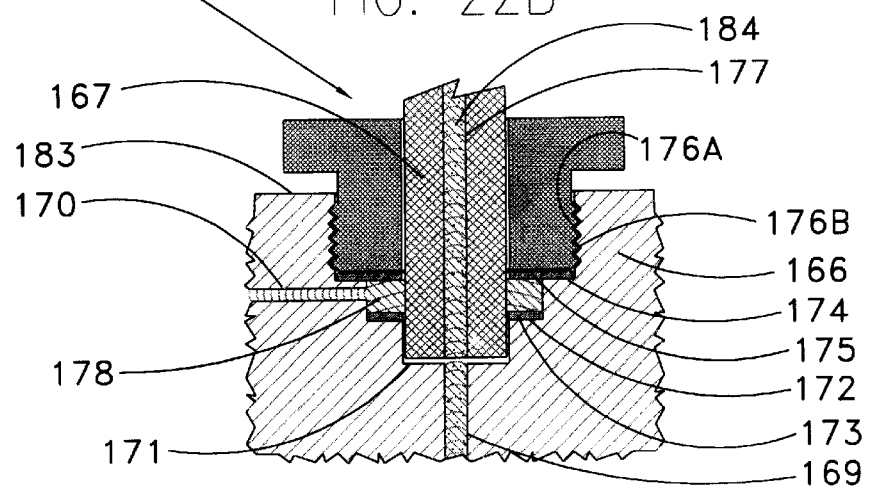

METHOD OF CONSTRUCTING A SAMPLER HAVING BARRIERS AND PASSAGES

STATEMENT OF CONTINUING APPLICATION

The present application is a continuation of U.S. patent application Ser. No. 08/701,406, filed Aug. 22, 1996, now U.S. Patent No. 5841036, entitled MODULAR SAMPLE CONDITIONING SYSTEM, listing as the inventor Donald P. Mayeaux.

TECHNICAL FIELD OF THE INVENTION

This invention relates to the analysis of fluids in a fluid process stream, such as implemented by petrochemical plants, refineries, gas separation plants, etc., and in particular to an in-stream sample collection and conditioning system which is easier to implement and maintain, more cost effective, and more reliable than existing systems.

The preferred embodiment of the present system contemplates a modular system adaptable to a variety of diverse configurations and criteria, the system having incorporated therein a base piece formed of interconnecting modular base members, the base piece having fluid passageways formed therein to provide fluid flow between the adjacent base member(s).

Situated adjacent to each of the modular base members forming the base piece are modular conditioning components, each selected from a field of diverse conditioning types and configurations, and adapted for the contemplated use, the system dispensing with the necessity of tubes, pipes, and traditional fittings. The present system as a whole provides a wholly new and unprecedented system for custom building fluid stream sampling and conditioning systems with heretofore unavailable "off-the-shelf" components.

The present invention further contemplates a unique and useful system for joining the various modular components forming the present system, in a manner which provides redundant leak resistance, flexibility in providing various conditioning configurations, and adaptability to diverse existing sampling stream interfaces.

Lastly, the preferred embodiment of the present invention contemplates a highly precise, low tolerance juxtaposition of the various components forming the present system, utilizing an extremely thin sheet formed membrane/gasket member, implemented in such a manner as to provide high thermocycling characteristics as well as high pressure tolerance, coupled with a low failure/leakage rate.

BACKGROUND AND PRIOR ART OF THE INVENTION

While the prior art has contemplated various and diverse systems for sampling and/or conditioning fluids in a process stream, said prior art systems tended to require a "custom" configuration for each site, entailing an expensive and time-consuming design, fabrication, and installation.

BACKGROUND

Overview of Sample Conditioning Systems

Processes as implemented in, for example, petrochemical plants, refineries, gas separation plants, etc. frequently require "on stream" analysis of process fluids, which are performed by analyzers located near the fluid sample source. Sample fluids flow directly from the source to the analyzer through an arrangement of piping and specialty components. This arrangement, referred to as a "sample conditioning system", is configured to extract fluid sample from the source; transport it to the analyzer; and, in the process, condition the fluid so that it is compatible with the analyzer.

Conditioning of the sample fluid by the sample conditioning system may consist of, for example:
(1) filtration to remove unwanted solids or liquids
(2) coalescing to remove aerosol droplets of liquids
(3) heating to prevent condensation of vapor
(4) flow and pressure control and measurement
(5) cooling to lower the sample dew point or remove unwanted liquid vapor.

The sample conditioning system may perform additional functions such as selection of one of several fluid streams for analysis by a single analyzer. This is called "stream selection" or stream multiplexing.

All of the components utilized for extracting, transporting, and conditioning the sample, as described previously, are part of the sample conditioning system. Some sample conditioning systems have components distributed along the entire distance between the source and the analyzer. Typically the largest concentration of these sample conditioning system components are located close together.

Reference to sample conditioning systems in the present invention are designed primarily for utilization in conjunction with closely grouped component arrangements, although the present system does include innovative features which could be useful for more spaced component arrangements. The components as implemented in the sample conditioning system, which are utilized for conditioning sample fluids, will hereinafter be referred to as conditioning components.

Current Construction of Sample Conditioning System

Current construction methods for Sample Conditioning System vary little from their first appearance several decades ago. Conditioning components are typically mounted on a vertical panel or shallow enclosure and are interconnected by tubing, piping, and fittings. Heavier conditioning components are mounted to the plate or enclosure with brackets while lighter conditioning components are supported by interconnecting fittings, piping, tubing, etc. Some Sample Conditioning System are further protected by "analyzer houses" or shelters which are usually large enough for maintenance technicians to work in and may also house process analyzers. Common to all of the above configurations is the fact that most Sample Conditioning Systems include a uniquely designed and implemented conduit system for conveying the fluid from the sample stream, and through the components, sometimes resulting in a maze of conduits, thereby resulting in high cost, maintenance, and the propensity for leakage from the system.

Problems Associated With Current Construction Methods

Several problems arise from the use of current construction methods. Some of the major problems are as follows:
(1) Excessive size—Sample Conditioning System produced by current construction methods require much space—a commodity which is very valuable in process areas. In general, lowering the size of analyzer houses or Sample Conditioning System enclosures results in significant cost reduction due to the high cost for space in process areas.
(2) Labor intensive—Configuring, mounting and interconnecting of conditioning components during the construction of a Sample Conditioning System is very labor intensive and therefore costly.

(3) Excessive Sample Conditioning System Internal Fluid Volume and Static Fluid Pocket Volume—It is well known in the industry that large internal volumes and static fluid pocket volume have a negative influence on the performance of Sample Conditioning System. The larger the internal volume and/or static fluid pocket volume in a Sample Conditioning System and the longer it takes to sweep it our after a sample fluid composition change occurs. Therefore Sample Conditioning System with large internal and/static fluid pocket volume require larger amounts of fluid to sweep, resulting in significant inefficiency.

In most cases it is desirable for fluid sample composition arriving at an analyzer to track closely the composition of the sample fluid at its source. In many instances the sample fluid utilized for sweeping cannot be returned to the source and therefore must be wasted. Therefore reducing the internal and static fluid cost related to loss of sample fluid and its environmentally safe disposition. Tube and pipe interconnections between conditioning components contribute the bulk of a Sample Conditioning System's internal volume. Fittings, especially pipe fittings, introduce static fluid pocket volume to the Sample Conditioning System.

(4) Safety and environmental concerns—It is common for sample fluid leaks to occur in conditioning component tubing and pipe interconnections and as a result of conditioning component failures. Examples of common conditioning component failures are: pressure regulator diaphragm ruptures and valve stem packing shrinkage due to wear or temperature changes. When fluid leaks occur, maintenance technicians can be exposed to toxic materials and fire or explosion hazard. Fluid used for continuously sweeping a Sample Conditioning System presents disposal problems and increases operational expenses.

PRIOR ART

While the prior art may have contemplated in some degree the utilization of block components having fluid passageways therethrough for fluid conditioning and/or conveyance, said prior art known to the inventor has been limited to hydraulics and other distinguishable configurations and applications.

For example, U.S. Pat. No. 3,831,953, issued 1974 to Leibfiitz et al contemplates a "Solenoid Operated Valve Assembly", teaching a "sealing unit adapted to be clamped between parallel faces of mating valve parts, comprising a sheet-like resilient gasket member engaged with one of said faces, and a uniform thickness plate member engaged with the other of said faces, said gasket member having apertures bounded one side only by lateral rib means which extend beyond the thickness thereof so that said gasket member is squeezed at the rib means between said parallel faces.

While the '953 device may contemplate a redundant leak isolating system (see col 5, lines 5–28, for example), the system fails to contemplate the overall method and apparatus of the present invention, as pertaining to modular sampling components. The system is clearly designed as valve assembly in a hydraulic system, and as such would not be able to be utilized in the present invention. Other differences between '953 and the present invention will be made clear in the discussion following infra.

GENERAL SUMMARY DISCUSSION OF THE INVENTION

Unlike the prior art, the present invention provides a cost effective, relatively easily implemented, reliable, and efficient system for in-stream sampling, adaptable to a variety of configurations and conditions.

The invention includes a method for:

(a) Constructing a sample fluid conditioning system utilizing modular base and modular conditioning components. This method eliminates tube and pipe interconnections and fittings. This reduces static fluid pocket volume and internal system volume, reduces mounting space requirements, and decreases the time and skill required to construct a sample conditioning system. It also decreases the time required for replacement of failed conditioning components.

(b) Constructing base and conditioning modules. The method further reduces internal and static fluid pocket volume of sample conditioning systems fabricated from modules constructed by this method. This method also provides a means for capturing and transporting to an external disposal system any sample fluids which would otherwise leak to the sample conditioning modules external environment as a result of fluid breaching a fluid barrier or failure of a conditioning component.

(c) Constructing fluid barriers between two surfaces. This method provides a means for leak-free communication of fluids between passageways of adjoining base and conditioning modules and also between passageways of adjoining base modules. This method of constructing fluid barriers also accommodates the capturing of leaks across a primary fluid barrier to prevent fugitive emission of sample fluid. The fluid barriers constructed by this method remain leak free even after thermocycling.

(d) Compressing fluid barrier material between two surfaces utilizing strain in a threaded member for supplying the required compressive force. This method compensates for displacement in the seal barrier material which would otherwise reduce the compressive force and permit fluid leaks.

(e) Retaining fluid barrier material utilizing beveled surfaces. This method permits the use of thin plastic or elastic fluid barrier materials and is less susceptible to displacement when thermocycled.

(f) Mounting modular base and modular conditioning components in a manner which provides the clamping force required for sealing of fluids.

(g) Attaching fluid transport tube to a base module in a manner that prevents sample fluid leaks to the surrounding environment in the event of a primary fluid barrier failure.

It is therefore an object of the present invention to provide a modular system for in-stream sampling of a fluid in a fluid sampling stream.

It is another object of the present invention to provide an in-stream sampling system which may be utilized in conjunction with a variety of system configurations and requirements, without the need for custom fluid conveyance means, such as piping, conduits or the like.

It is still another object of the present invention to provide a system for in-stream sampling, comprising a modular base member adapted to have situated thereupon, in fluid impermeable fashion, a diverse assortment of communicating fluid conditioning modules.

It is still another object of the present invention to provide a redundant leak sealing means to prevent fugitive emissions.

It is still another object of the present invention to provide an ultra-thin gasket sealing system configured to provide high thermocycling tolerances, and perform satisfactorily in a broad range of temperature extremes.

Lastly, it is an object of the present invention to provide an ultra-thin gasket sealing system configured to provide an effective, low maintenance, high-pressure seal.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 4 consists of a cross sectional view taken along line I,I of FIG. 1. This view includes a cross sectional view of an adjacent base module and collection passage grooves not shown in FIG. 1.

FIG. 4A provides a detail of the junction where the conditioning component module and base module contact the fluid barrier. This view shows the surface segments of each module in contact with the fluid barrier.

FIG. 4B and 4C sets forth details showing where passages from two modules in conjunction with surface segments and fluid barrier segments form a sealed passage junction.

FIG. 5 provides a cross sectional view taken along line II,II of FIG. 1. This view includes a cross sectional view of passages and grooves.

FIG. 5A illustrates a detail of the junction where conditioning component module and base module contact the fluid barrier. This view shows the surface segments of each module in contact with the fluid barrier.

FIG. 5B is a figure showing in detail where passages from two modules, in conjunction with surface segments and fluid barrier segments, form a sealed passage junction.

FIG. 22A is an isometric cross sectional exploded view of a nut, two ferrules, a length of tubing and a threaded module segment.

FIG. 22B provides an isometric cross sectional assembled view of FIG. 22A showing passages and cavities.

DETAILED DESCRIPTION OF THE INVENTION

The preferred embodiment of the present invention includes a novel method for constructing sample conditioning systems. Said method simplifies construction, reduces construction time, improves performance, is safer to operate and maintain and essentially eliminates fugitive sample fluid emissions to the environment. In this method, conditioning components such as valves, pressure regulators, flowmeters and filters are constructed in a modular fashion.

Figure 1:
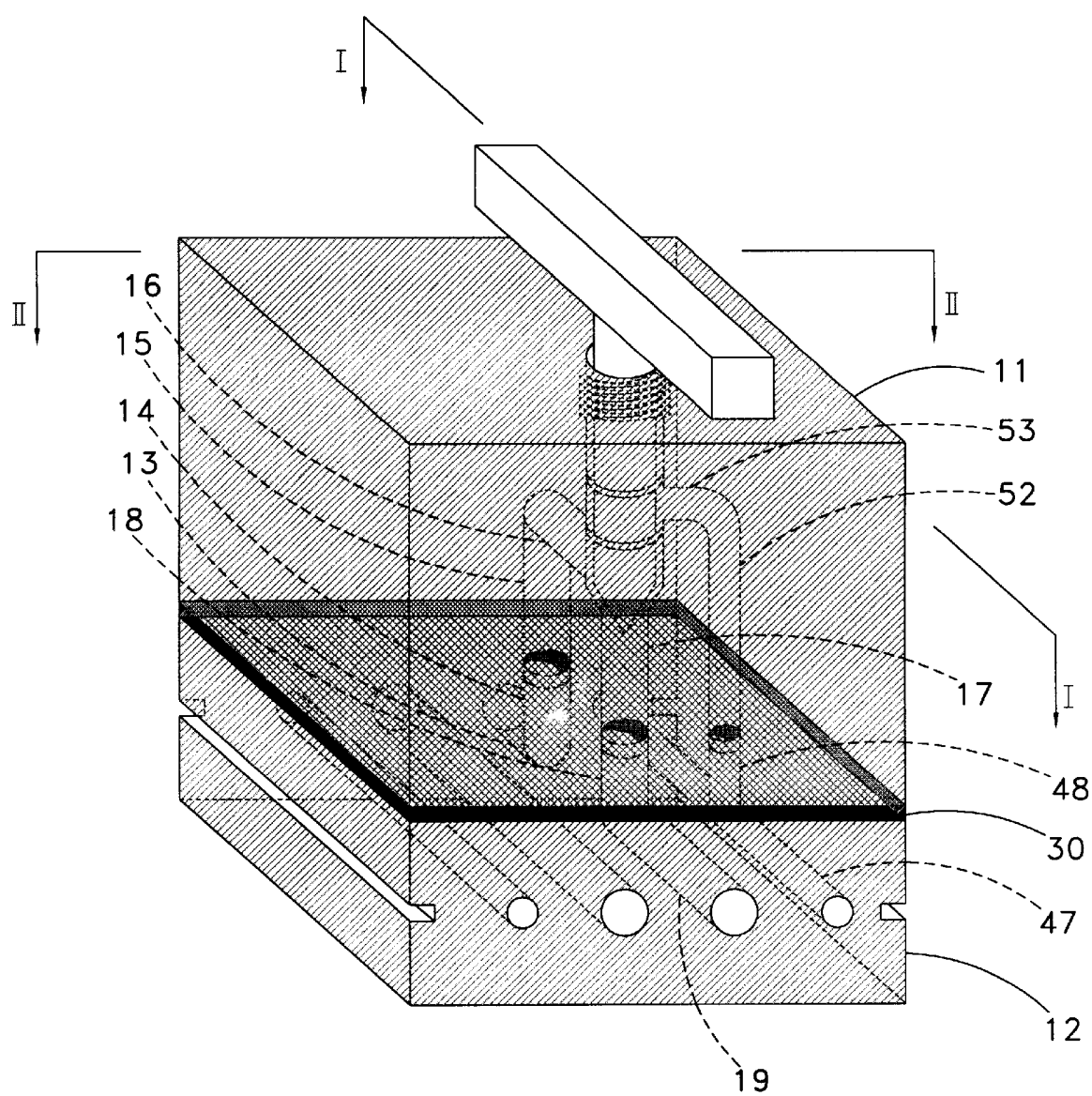
FIG. 1 illustrates an isometric view of a component conditioning module mounted to a base module. The internal passages, fluid barrier material and valve are shown. Grooved passages on the module surfaces are not shown.

The conditioning component modules are mounted to a modular base, as shown in the block having conduits formed therein in FIG. 1. In FIG. 1, the conditioning component module 11, shown, is designed to perform a valve function, and is shown mounted to base module 12. The present invention provides for essentially all types of conditioning components to be made modular and mounted to base modules such as (12), above, and is not limited to the conditioning component having a valuing function as illustrated in FIG. 1.

Figure 2:
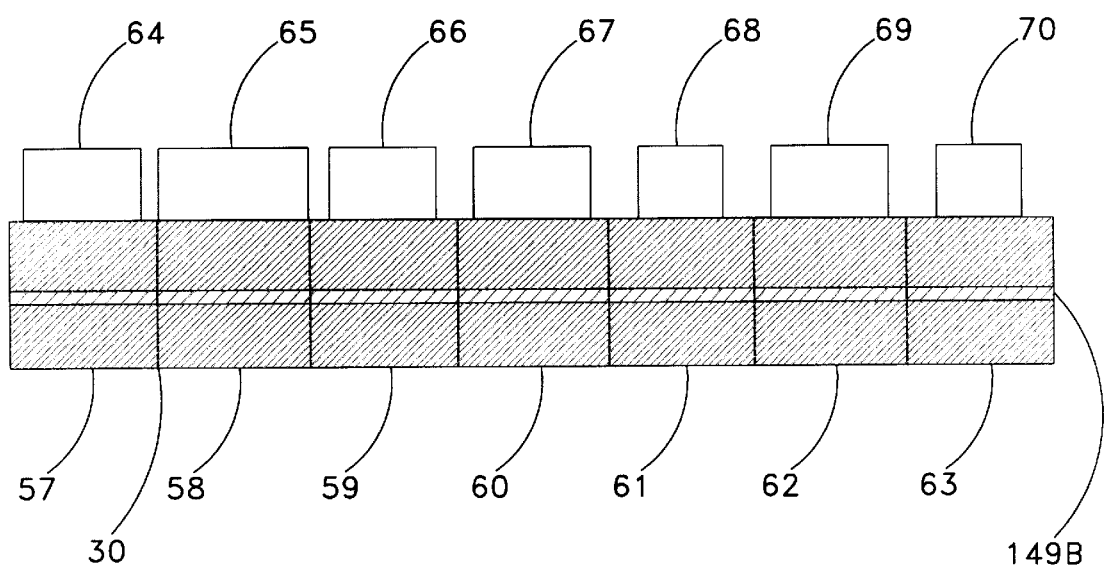
FIG. 2 illustrates a side view of a plurality of conditioning component modules mounted to base modules, assembled side by side with fluid barrier material between adjacent modules.

Base modules with mounted conditioning modules are then arranged in a side by side fashion as shown in side view FIG. 2. In FIG. 2, base modules 57, 58, 59, 60, 61, 62, and 63 can be seen in a side by side arrangement with mounted conditioning components 64, 65, 66, 67, 68, 69 and 70. A means, not shown in FIG. 2, retains the modules in their side by side orientation and provides for mounting of the entire module assembly. Internal passages in conditioning component modules and base modules conduct sample fluid through the network of conditioning components in accordance to predetermined fluid flow requirements. Novel-fluid barrier means between base modules and between base modules and component modules prevent undesired fluid flow between internal passages and also prevent fluid leaks to the environment.

Fluid passes directly from a passage in one module to a passage in another module without the need for interconnecting pipes, tubing or fittings, via the base member, which conveys the fluid via conduits formed therein to adjacent conditioning modules, which mount upon the base at aligned, predesignated conduit coordinates. Because there is no need for excessive piping, the present system provides an efficiency which aids in simplifying the construction task, reduces overall cost, and significantly improves function by eliminating static fluid pocket volume and reduces sample conditioning systems internal volume.

Prior art methods of construction relate primarily to pneumatic and hydraulic fluid control modules, such as shown in U.S. Pat. No. 3,831,953, discussed infra while the preferred embodiment of the present invention addresses problems associated with sample fluid conditioning for analysis by automated analyzers. The needs are very different. For example, of prime importance in sample fluid conditioning is the need for minimal internal system volume, and the absence of static fluid pocket volume. This is not a requirement in typical pneumatic or hydraulic fluid control devices. Another example is the need in sample fluid conditioning systems for minimizing or eliminating fugitive fluid emissions resulting from fluid leaks which also is not a usual requirement for pneumatic or hydraulic fluid control devices.

The method of utilizing conditioning component modules and base modules in the particular manner hereafter described allows conditioning component modules to be designed and constructed without compromise with regard to the need for fluid communication between and among other conditioning component modules. With this method, internal fluid passages in conditioning components modules need only mate at any point along appropriate horizontal passages in the base modules. These horizontal fluid passages in all of the base modules may be standardized with regard to location of the openings which communicate sample fluid to adjacent base modules. The task of designing passages in conditioning component modules to mate with horizontal passages in the base module is substantially easier than designing conditioning component modules which intercommunicate, without use of base modules, with adjacent conditioning component modules.

Schematic Flow Diagram

Figure 3:
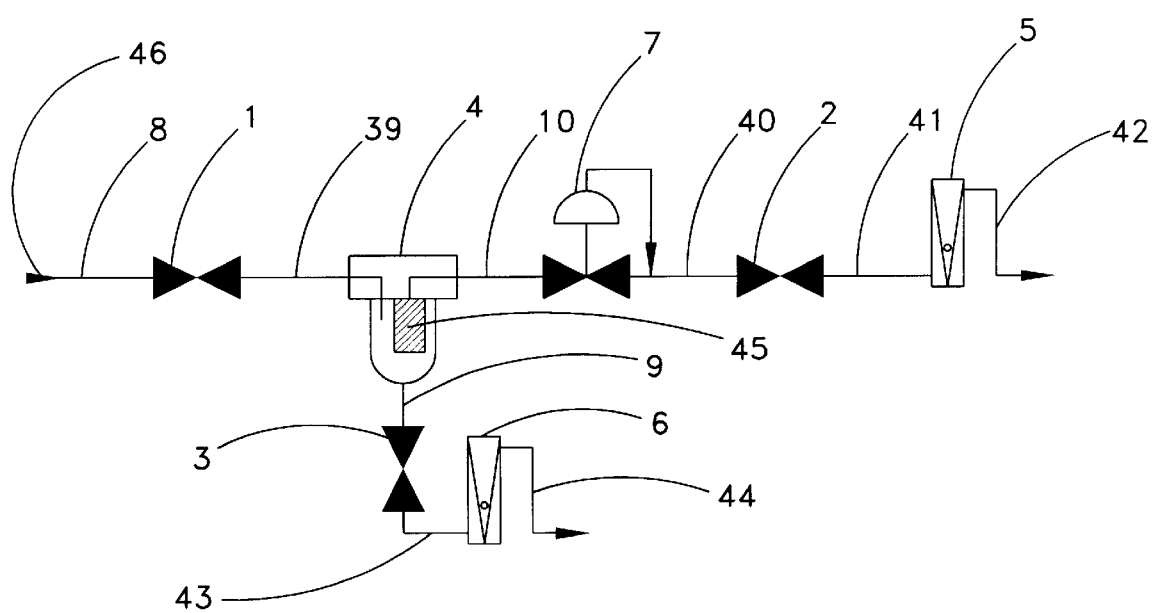
FIG. 3 provides a schematic flow diagram of a typical sample conditioning system.

Prior to constructing a sample conditioning system utilizing component conditioning modules and base modules, one must first establish a schematic flow diagram. An example of such a diagram, as seen in FIG. 3, must include the conditioning components, such as valves 1, 2, and 3; filter 4, flow meters 5, and 6; and pressure regulator 7, which will be required to provide the desired sample fluid conditioning for a specific, exemplary application. The fluid communication circuits between conditioning components should also be indicated by the schematic flow diagram. In the schematic flow diagram of FIG. 3 there are three fluid circuits. The first fluid circuit is comprised of passage 8 valve 1 and passage 39. The second fluid circuit is comprised of a portion of filter 4 which includes filter element 45, passage 10, pressure regulator 7, passage 40, valve 2, passage 41, flowmeter 5, and passage 42. The third fluid circuit consist of a portion of filter 4, passage 9, valve 3, passage 43, flowmeter 6 and passage 44.

It should be noted that the schematic flow diagram of FIG. 3 is an example of a typical sample conditioning system. However, the invention applies to all types of sample conditioning system some of which maybe substantially more complex and include conditioning components not shown in FIG. 3.

In normal operation of the sample conditioning system of FIG. 3, sample fluid enters at entrance 46 of passage 8 then flows through the first fluid circuit. The first fluid circuit flow then branches into the second and third fluid circuits upon entering filter 4. Fluid exits the second fluid circuit from passage 42 into an analyzer not shown. Fluid exits the third fluid circuit from passage 44 to a safe disposal system not shown. The fluid flow rate through the first fluid circuit is equal to the sum of the fluid flow rates of the second and third fluid circuits. The purpose of the second fluid circuit is to condition sample fluid so that it is compatible with a given analyzer. In this particular case the fluid is filtered by filter element 45, fluid pressure is controlled by pressure regulator 7, fluid flow rate is controlled by valve 2, and flow rate is monitored by flowmeter 5. Passages 10, 40, 41, and 42 provide fluid interconnections between conditioning components.

The amount of time required for sample fluid to be transported from a source to an analyzer is commonly referred to as the system lag time. The system lag time represents the minimum time required for an analyzer to respond to a composition change at the sample fluid source. Fluid flow rate through the sample conditioning system has a direct impact on system lag time.

The purpose of the third fluid circuit is to aid in adjusting the total fluid flow rate in the first fluid circuit. Altering the flow rate of the third fluid circuit using valve 3 changes the fluid flow rate of the first fluid circuit and subsequently impacts the system lag time. The fluid circuit arrangements and conditioning components which can be included in a sample conditioning system are not limited to those referenced in FIG. 3. The schematic flow diagram established need not be tangible. A mental, computer generated, or any other means for establishing a schematic flow diagram containing the aforementioned information will suffice. The purpose for the schematic flow diagram is to aid in the selection of component conditioning modules and base modules which will be utilized in the construction of a modular sample conditioning system.

Mounting a Conditioning Component Module to a Base Module and the Resulting Typical Fluid Flow Paths After a schematic flow diagram has been established the required component conditioning modules, which have been designed to perform specific sample fluid conditioning functions, are mounted to their respective base modules. An example of this is seen in FIG. 4 where a component conditioning module 11, designed to perform a fluid metering valve function, is mounted to base module 12. Base modules are specifically designed to provide the fluid communication with the component conditioning module to which it is mated and other conditioning component modules and base modules. Base modules also provide fluid communication between other base modules and component conditioning modules. In the example shown in FIG. 4 it can be seen that sample fluid 122 entering base module 12 at passage opening 20, flows through passage 13, passage 14, passage opening 21, opening 28 in fluid barrier material 30, enter component conditioning module 11, at passage opening 22, flow through vertical passage 15, horizontal passage 16, valve cavity 31, vertical passage 17, exit the component conditioning module 11 at the passage opening 23, flow through opening 29 in seal barrier material 30, re-enter base module 12 at passage opening 24, flow through vertical passage 18, horizontal passage 19, exit base module 12 at passage opening 33 and enter adjacent base module 12A.

The metering valve 25 comprised of valve stem 27, stem tip 32, and valve seat 26 operates in a conventional manner, thus by rotating valve stem 27 the action of male thread 38A and female thread 38B causes the stem tip 32 to change its position relative to valve seat 26 which in turn alters the resistance to fluid flowing through valve cavity 31. FIG. 4 illustrates how sample fluid flows through a typical component conditioning module and base module combination.

From this example it can be clearly seen that it is possible to mount many different types of component conditioning modules to base modules, and that in a similar manner sample fluid can be transported from a first passageway opening in the base module, through internal passages of the base module, into a component conditioning module for the purpose of performing a specific sample fluid conditioning function, re-enter the base module exit through a second passage opening in the base module and thereon flow into an adjacent base module.

Containment of Fluid Leaks Across a Primary Fluid Barrier

Many conditioning components designed by prior art methods are susceptible to leakage of fluids to the environment which is generally referred to as fugitive emissions. Typical sources of fluid leaks in conditioning components are damaged static fluid barriers, dynamic fluid barriers, and fluid containment barriers such as diaphragms in pressure regulators. Other common sources of fluid leaks to the environment in prior art are threaded pipe and tube interconnecting fittings. The invention prevents fluid leaks of all sources from entering the environment. It accomplishes this by capturing the leaking fluid and transporting it to an external site. FIG. 5 illustrates how, in the case of a dynamic fluid barrier failure, leaking fluid 187 is captured and transported to the base module 12's fluid containment passage 47.

Under normal operation lower stem fluid barrier 56 prevents sample fluid 122 from entering the fluid containment network of base module 12 and component conditioning module 11 which is comprised of cavity 54, passages 53, 52, 48, and 47. Upper stem fluid barrier 55 is a barrier between the external environment and cavity 54.

Figure 6:
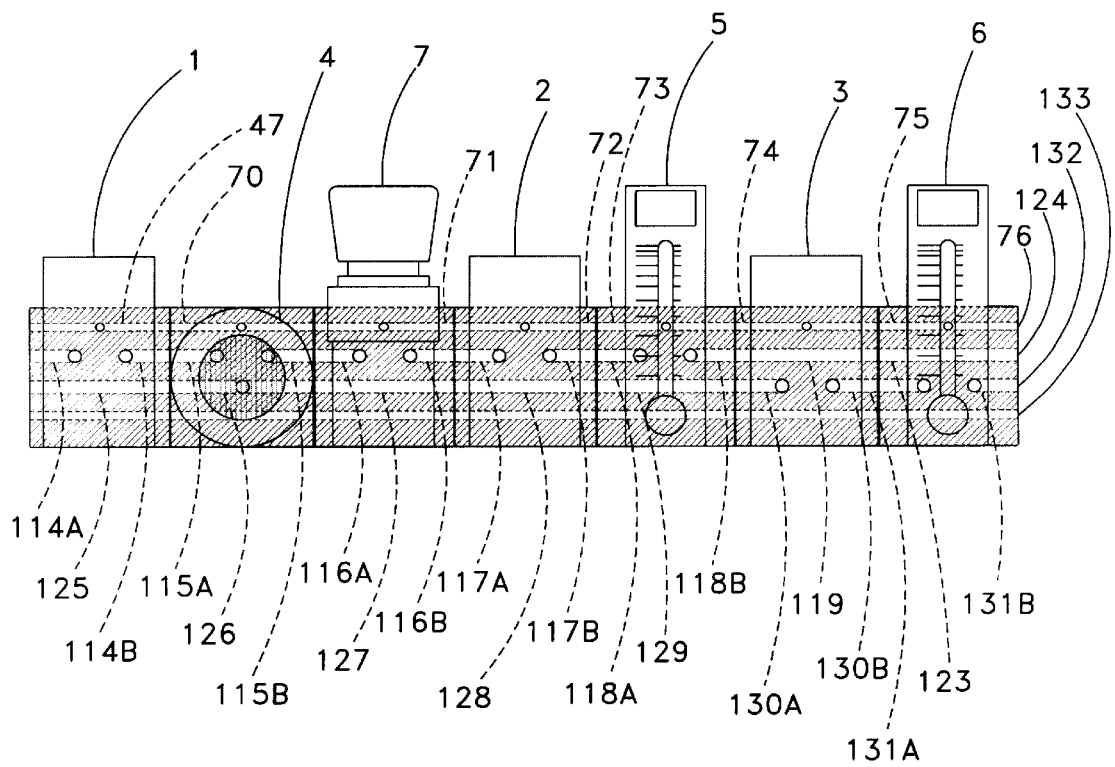
FIG. 6 is a cross sectional top view of a plurality of conditioning component modules and base modules showing horizontal passages for fluid communication between the base module and conditioning component module. This arrangement performs the functions illustrated in FIG. 3.

In the event of a lower stem fluid barrier 56 failure, sample fluid 122 enters cavity 54, flows through horizontal passage 53, vertical passage 52 and vertical passage 48 into horizontal passage 47 where it is subsequently transported, by way of the sample conditioning system's fluid containment network to an external disposal site. Upper stem fluid barrier 55 prevents sample fluid 122 in cavity 54 from leaking to the external environment. The Sample Conditioning System's fluid containment network is comprised of horizontal passages 47 and corresponding passages in other base modules of the Sample Conditioning System. When base module with mounted conditioning component modules are assembled side by side as shown in FIG. 6, the vent collection passage of each base module mechanically align and are in fluid communication.

Together fluid containment passages 47, 70, 71, 72, 73, 74, and 75 of assembled base modules comprise the Sample Conditioning System's fluid containment network 76. When Sample Conditioning System's fluid containment network 76 is in fluid communication with an external disposal site not shown, sample fluid 187 captured in any of the conditioning component module and base modules fluid containment networks will be transported and vented to the external disposal site.

The fluid containment network of a conditioning component module and base module mating combination may collect sample fluid leaks from a plurality of sources. In all such cases however, the captured leaking fluid will be transported to the conditioning component module and base module's fluid containment passage where it will ultimately be vented to the external disposal site by way of the Sample Conditioning System fluid containment network 76.

It should be noted that the Sample Conditioning System's fluid containment network 76 is normally maintained at a pressure lower than the sample fluid pressure in conditioning component module and base module. Typically the fluid containment network 76 pressure is within 5 PSI of atmospheric pressure. The differential pressure across upper stem fluid barrier 55 being typically less than 5 PSI reduces the risk of sample fluid breaching this fluid barrier.

In order for sample fluid to leak to the atmosphere, lower stem fluid barrier 56 and upper stem fluid barrier 55 would have to fail simultaneously. If in some cases sample fluid leaking to the atmosphere presents an excessive hazard, then the Sample Conditioning System fluid containment network 76 should be maintained at sub atmospheric pressure. This will insure that if upper stem fluid barrier 55 is damaged sample fluid will not flow to the atmosphere, instead, gas from the surrounding environment will flow into the Sample Conditioning System fluid containment network. In a similar manner other types of dynamic fluid barriers and static fluid barriers can be prevented from leaking sample fluids to the environment when a fluid barrier failure occurs.

The junction where two passage openings, located on separate conditioning components module's or base modules, are in fluid communication are called passage junctions. A typical passage junction 95 is seen in FIG. 5. Passage opening 49, fluid barrier opening 50, and passage opening 51 in combination comprise passage junction 95. Passage junctions must be sealed to prevent sample fluid from leaking to the external environment or into other passage junctions.

Figure 7:
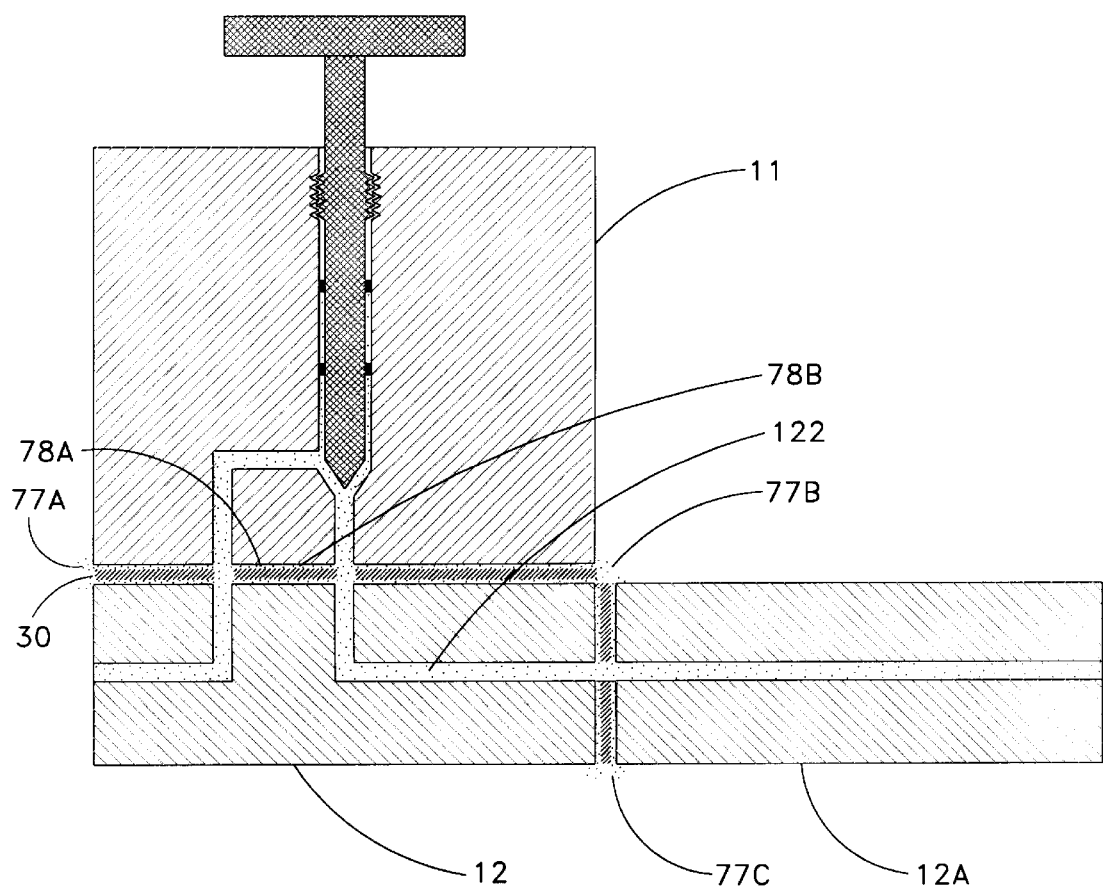
FIG. 7 is a cross sectional view taken along line I,I of FIG. 1 including an adjacent base module not shown in FIG. 1. This view does not include collection grooves shown in FIG. 4 and demonstrates how fluid can teak to the surrounding atmosphere.

It can be seen in FIG. 7 that without special provisions fluid 122 contained in passages of may be and base modules 12 and 12A can leak from a passage junction into the environment; such as is seen at 77a, 77b, and 77c; or into other passage junctions as seen at 78a, and 78b. From FIG. 7 it can also be seen that fluid leaks could occur on both sides of fluid barrier material 30 if precautions were not otherwise taken.

Therefore the method of sealing to prevent fluid leaks from occurring at passage junctions must protect against fluid leaks which could arise on either or both sides of seal barrier material 30. The invention includes a special method for sealing around passage junctions which are between conditioning component module and base module and also passage junction which are between two adjacent base module's. The passage junction sealing method of the invention provides two series fluid barriers separated by a collection passage on both sides of fluid barrier material 30.

The following method describes the preferred embodiment for construction of a static fluid barrier between a conditioning component module and a base module such method providing, on both sides of the fluid barrier material, two series seal separated by a collection passage in fluid communication with an external disposal site.

Figure 8:
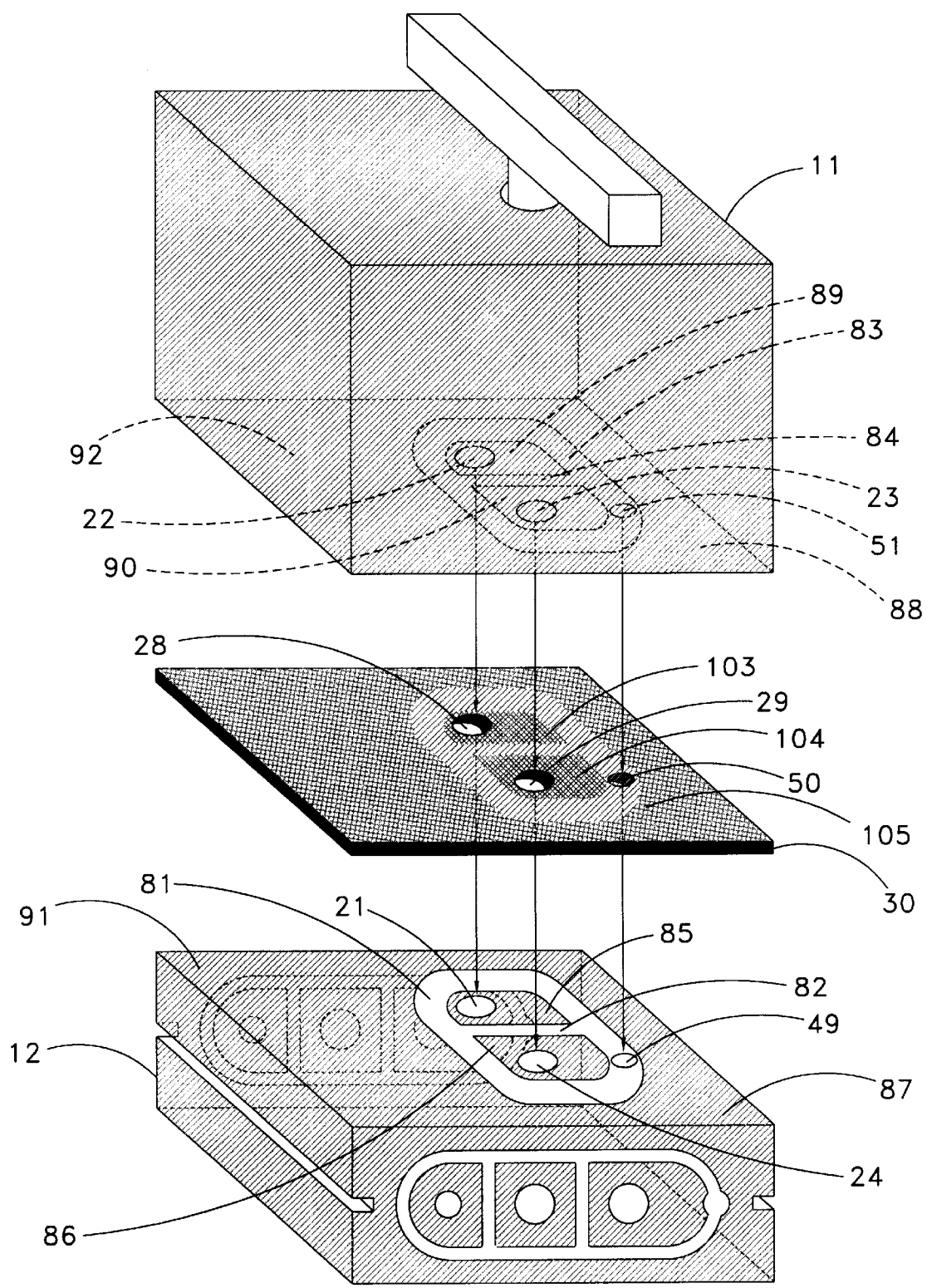
FIG. 8 provides an exploded isometric view of a conditioning component module, fluid barrier material and base module. The grooved surfaces, passage openings, and fluid barrier openings are shown, passages and the internal portion of the valve are not shown.
Figure 9:
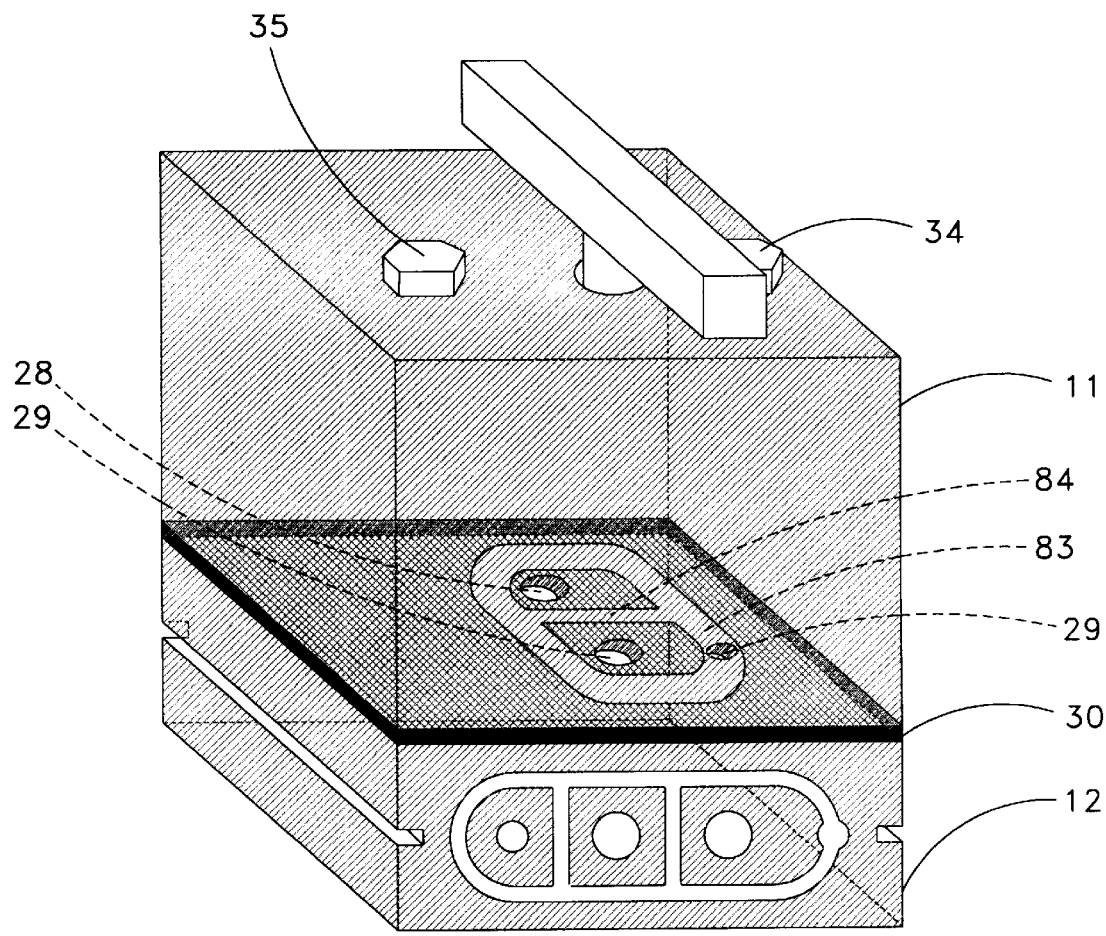
FIG. 9 is an assembled isometric view of FIG. 8 including the exterior view of the bolts which hold the assembly together.
Figure 10:
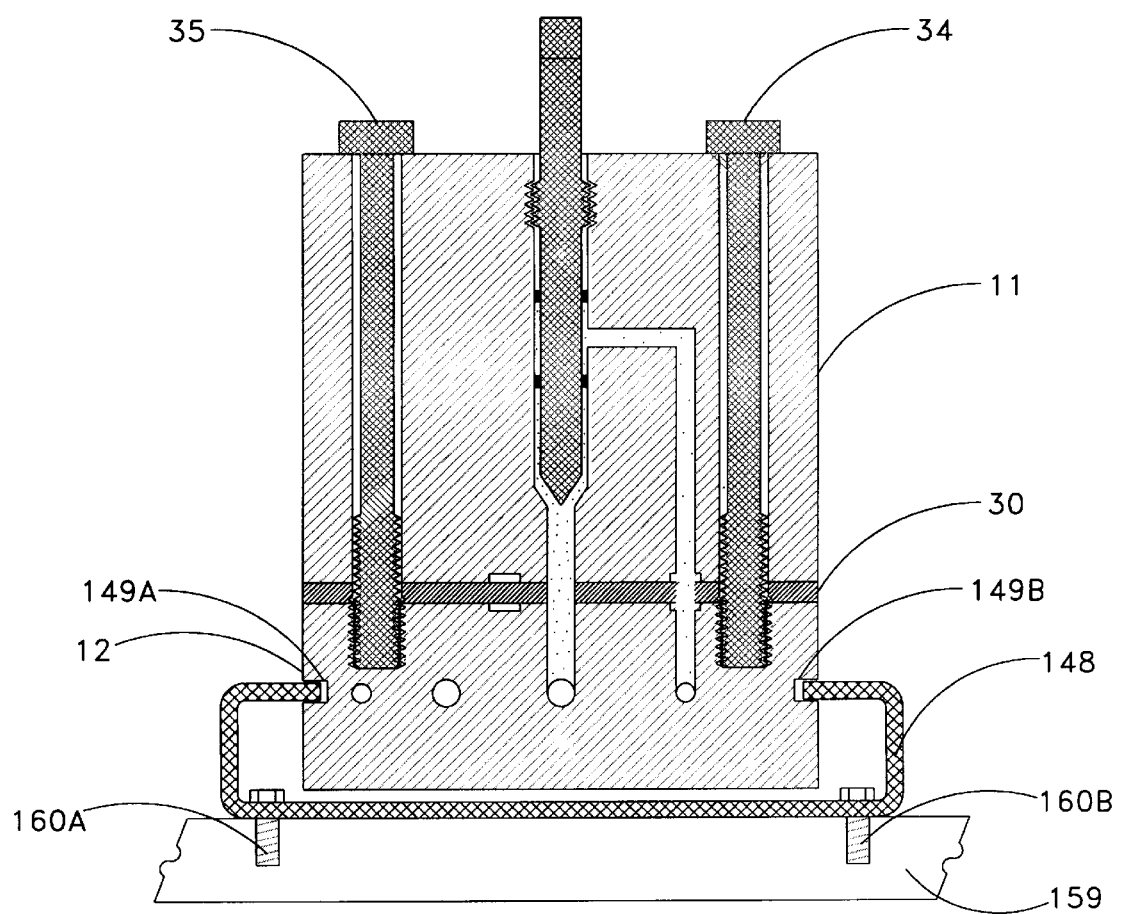
FIG. 10 is a view of the invention of FIG. 5, showing a cross section of the assembly bolts, mounting rail, mounting surface, and screws retaining assembly to the mounting surface.

Referring to FIGS. 8, 9, and 10, the method consists of the following:

A first passage groove 81 (FIG. 8) is formed in the surface 91 of base module 12 surrounding passage openings 21 and 24 and intersecting passage opening 49.

A second passage groove 82 is formed which intersects opposite sides of passage groove 81, and passes between passage openings 21 and 24. Passage grooves 81 and 82 are formed in a manner that will provide a space 86 surrounding passage opening 24; a space 85 surrounding passage opening 21; and a space 87 surrounding passage groove 81.

A third passage groove 83 is formed in the under surface 92 of conditioning component module 11 surrounding passage openings 22 and 23 and intersecting passage opening 51.

A forth passage groove 84 is formed which intersects opposite sides of passage groove 83 and passes between passage openings 22 and 23, passage grooves 83 and 84 are formed in a manner that will provide a space 90 surrounding passage openings 23; a space 89 surrounding passage openings 22; and a space 88 surrounding passage groove 83.

Conditioning component module 11 is then mounted to base module 12 (FIG. 9 and 10). When mounted as shown in FIG. 9, passage grooves 83 and 84 in conditioning component module 11 are in approximate alignment and have the same approximate shape and geometry as passage 81 and 82 of base module 12, In the preferred embodiment a fluid barrier material 30 is inserted between conditioning component module 11 and base module 12, Bolts 34 and 35 secure the alignment between conditioning component 11 and base module 12. Other fastening means may be used for this purpose. Openings 28 (FIG. 4, 5, 8, and 9) in the fluid barrier allows fluid to flow between passages 14 and 15; opening 29 allows fluid to flow between passages 17 and 18; and opening 50 (FIG. 5) allows fluid to flow between passages 48 and 52.

By tightening bolts 34 and 35 (FIG. 10) conditioning component module 11 and base module 12 apply a force to opposite sides of fluid barrier material 30. The first fluid barrier 96 (FIG. 4, 4A, 4B, 4C, 5, and 8) around the passage opening junction 93; comprised of passage openings 21, fluid barrier opening 28 and passage opening 22; is formed by space 85 on base module 12, space 89 on conditioning component module 11 and the segment 103 of fluid barrier 30 which is sandwiched directly between space 85 and 89. The first fluid barrier 96 is surrounded by segments of groove 81 and groove 82 on base module 12 and grooves 83 and 84 on conditioning component module 11.

The second fluid barrier 97 around passage opening junction 93 is formed by space 86, 87, 88, and 90 and the segment of fluid barrier 104 material sandwiched directly between spaces 86 and 90; and segment of fluid barrier material 105 between space 87 and 88. Passage grooves 81, 82, 83, and 84, in combination, surround passage opening junction 93 on both sides of fluid barrier 30, in a manner that divides the first fluid barrier 96 and second fluid barrier 97 of passage opening junction 93. In the event that sample fluid breaches the first fluid barrier 96 encircling passage opening junction 93, on either or both sides of fluid barrier 30, passage grooves 81, 82, 83, and 84 will capture the fluid and transport it to passage junction 95; comprised of passage opening 49, passage opening 51, and fluid barrier opening 50; into passage 48 then into horizontal passage 47 where it will be subsequently vented to an external disposal site as previously described. The second fluid barrier 97 in the event of a leak contains fluid within the passage grooves 81, 82, 83, and 84 preventing it from leaking to the surrounding environment or into adjacent passage junction 94.

The first fluid barrier 98 around passage junction 94; comprised of passage opening 24, fluid barrier opening 29, and passage opening 23, is formed by space 86 on base module 12, space 90 on conditioning component module 11, and the segment 104 of fluid barrier 30 which is sandwiched directly between space 86 and 90.

The second fluid barrier 99 around passage junction 94 is formed by space 85, 87, 88, and 89 and the segment of fluid barrier 105 sandwiched between space 88 and 87; and segment of fluid barrier 103 sandwiched between space 85 and 89. Passage grooves 81, 82, 83, and 84 in combination surround passage opening junction 94, on both sides of fluid barrier 30 in a manner that divides the first fluid barrier 98 and second fluid barrier 99 of passage opening junction 94.

In the event that sample fluid breaches the first fluid barrier 98 encircling passage opening junction 94, on either or both sides of fluid barrier 30, passage grooves 81, 82, 83, and 84 will capture the fluid and transport it to passage junction 95, into passage 48, then into horizontal passage 47 where it will be subsequently vented to an external disposal site as previously described.

As an alternate means, collection passage grooves may be formed in the fluid barrier material in special cases. However, in the preferred embodiment collection passage groves are formed on the surface of the conditioning component module and base module as previously described. Fluid barrier 100 prevents fluid communication between the external environment and passage junction 95; and between the external environment and groove 81 and 83. Passage junction 95 is comprised of passage opening 49, fluid barrier opening 50, and passage opening 51. Fluid barrier 100, is formed by space 87 on base module 12, space 88 on conditioning component module 11, and the segment 105 of fluid barrier material 30 which is sandwiched between space 87 and space 88. Seal barrier segment 105, when conditioning component module 11 is mounted to base module 12 and fluid barrier material 30 is inserted between, surrounds passage groove 83 of the conditioning component module 11, passage groove 81 of base module 12, and vent passage junction 95.

Effects of Fluid Barrier Thickness and Clamping Force on Prevention of Fluid Barrier Breach It can be seen in FIG. 10 that by turning screws 34 and 35 in a direction which will increase thread engagement, that an increasing amount of force can be applied to the opposite sides of fluid barrier material 30 by conditioning component module 11 and base module 12. In the preferred embodiment the combined force applied by screws 34 and 35 is sufficient to overcome the opposing force resulting from the internal fluid pressure in conditioning component module 11 and base module 12 plus apply approximately 2000 pounds per square inch additional clamping pressure to their surface which is in contact with the opposite sides of fluid barrier material segments 103, 104, and 105. The absolute amount of clamping force applied to fluid barrier material segments 103, 104, and 105 to effect containment of sample fluids as previously described will depend upon the type of fluid barrier material 30 utilized and its thickness, and the range that the temperature of the fluid barrier 30 is cycled during the course of its service life.

It is highly desirable in a sample conditioning system that its material of construction are inert. Therefore and ideal fluid barrier material 30 is a sheet of TEFLON® plastic. It is well known in the prior art that fluid barriers constructed from TEFLON® plastic are susceptible to leakage due to plastic displacement, especially when its temperature is cycled through a wide range at elevated temperatures.

This is overcome in the present invention by several means. First, in the preferred embodiment, fluid barrier material thickness is minimized and preferably less than 0.040 inches and more preferably less than 0.010 inches. By minimizing the thickness of fluid barrier material 30, compensation for its plastic displacement can be more easily effected. Although many means exist to compensate for fluid barrier material 30 plastic displacement, the preferred means are by pre-loading bolts 34 and 35 to produce a strain of a value equal to or exceeding the maximum potential reduction of thickness of fluid barrier material 30 resulting from plastic displacement.

It has been well established by prior art that bolts may be safely torqued to produce a stress equal to approximately 60% of the bolts tensile strength In the preferred embodiment 304 stainless steel is utilized, however, many other types of material may be used for this purpose. The tensile strength of 304 stainless steel is approximately 92,000 pounds per square inch. At 60% of this value, which is 55,200 pounds per square inch, the strain is approximately 0.0018 inches per inch of free bolt length. The free bolt length is defined as the portion of bolt 34 and 35 which is not engaged in female thread. Minimizing the thickness of fluid barrier material 30, minimizes the plastic deformation compensation requirement for fluid barrier material 30.

The minimum thickness at which fluid barrier material 30 can still effectively function as a fluid barrier is dependent upon the surface roughness of surface 92 of conditioning component module 11 and surface 91 of base module 12.

Through experimentation it was found that a fluid barrier material thickness of 0.005 inches was effective in sealing machined surfaces with roughness of 64 micro inches. It was also empirically determined that when Teflon® is the fluid barrier material 30 an initial net clamping force of 2000 pounds per square inch applied across opposite sides of fluid barrier surface is required to contain or seal without leakage fluids which are under a pressure of 1000 pounds per square inch. The net clamping force is defined as the clamping force applied to the fluid barrier material exclusive of the opposing force resulting from internal fluid pressure.

It was also determined that when Teflon® is the fluid barrier material 30, a net clamping force of 500 pounds per square inch applied across opposite sides of fluid barrier surface is required to contain or, seal without leakage, fluids which are at a pressure no greater than 50 pounds per square inch. From this it was concluded that a minimum of 500 pounds per square inch clamping force was required to effect sufficient plastic displacement of the Teflon® fluid barrier material 30 to fill and seal surface irregularities of surfaces 91 and surface 92. Clamping forces were for the most part applied and measured by means of torque gauge at ambient temperatures ranging from 70° F.–75° F.

When constructing a fluid barrier according to the invention observe the following steps for selecting and forming fluid barrier material 30 and also to select and tighten the bolts which apply the net clamping force to both sides of fluid barrier material 30.

(a) Select a sheet of fluid barrier material 30. Preferably the thickness is approximately 0.005 inches.
(b) Shape the exterior of the selected sheet of fluid barrier material 30 to conform approximately with the exterior shape of base module 12 and conditioning component module 11.
(c) Form openings through the sheet of fluid barrier material 30 which will provide fluid communication between corresponding passages of base module 12 and conditioning component 11.
(d) Select the number and diameter of bolts which will supply the required clamping force between opposite side of the fluid barrier material 30, when torqued to approximately 60% of the bolts tensile strength.
(e) Select bolt lengths which will, when torqued to 60% of tensile strength, result in a strain equal to or greater than the thickness of the fluid barrier material 30.

Reducing the effective fluid barrier area reduces the number and/or size of bolts required to produce the desired clamping force. This can be easily done by reducing the area of the surface 91 and 92 which contact and apply clamping force to segments of fluid barrier material 30. Forming a depression of 0.010 inches to 0.015 inches in the surface of 91 and 92 where contact with the fluid barrier material 30 is not desired can be used as a means for reducing the effective fluid barrier contact area which in turn reduces the clamping force required.

Figure 11:
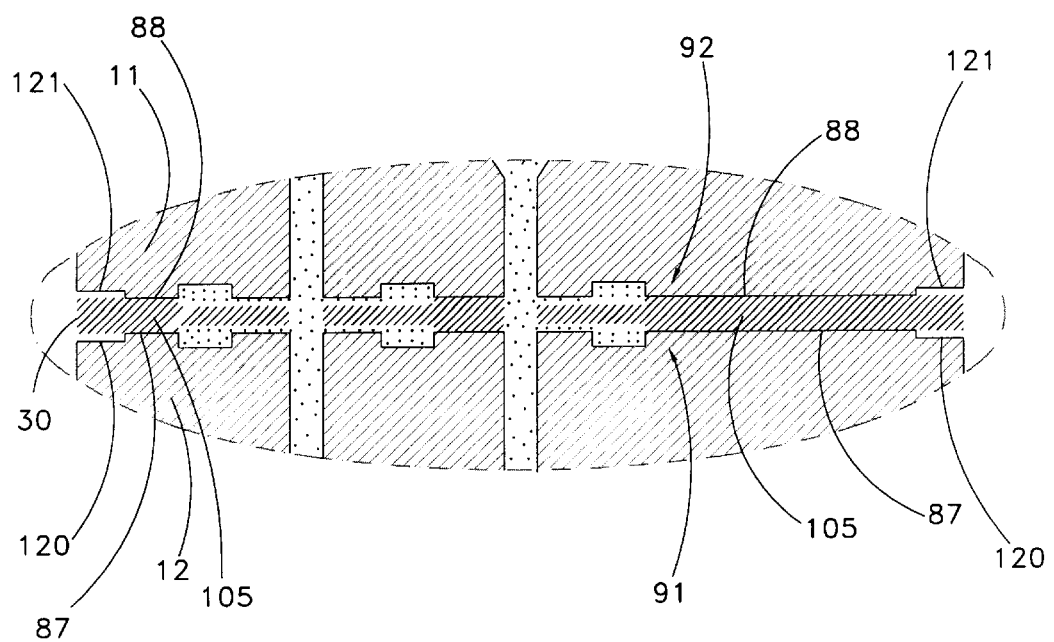
FIG. 11 is a modification of FIG. 4A showing a depression in the surfaces of the conditioning component module and base module for the purpose of reducing contact area with the fluid barrier material.

As an example in FIG. 11 a surface depression 120 is formed in space 87 of surface 91 and a surface depression 121 is formed in space 88 of surface 92. Depression 120 reduces the area of space 87 which contacts segment 105 of fluid barrier material 30 and depression 121 reduces the area of space 88 which contacts segment 105 of fluid barrier material 30.

Figure 12:
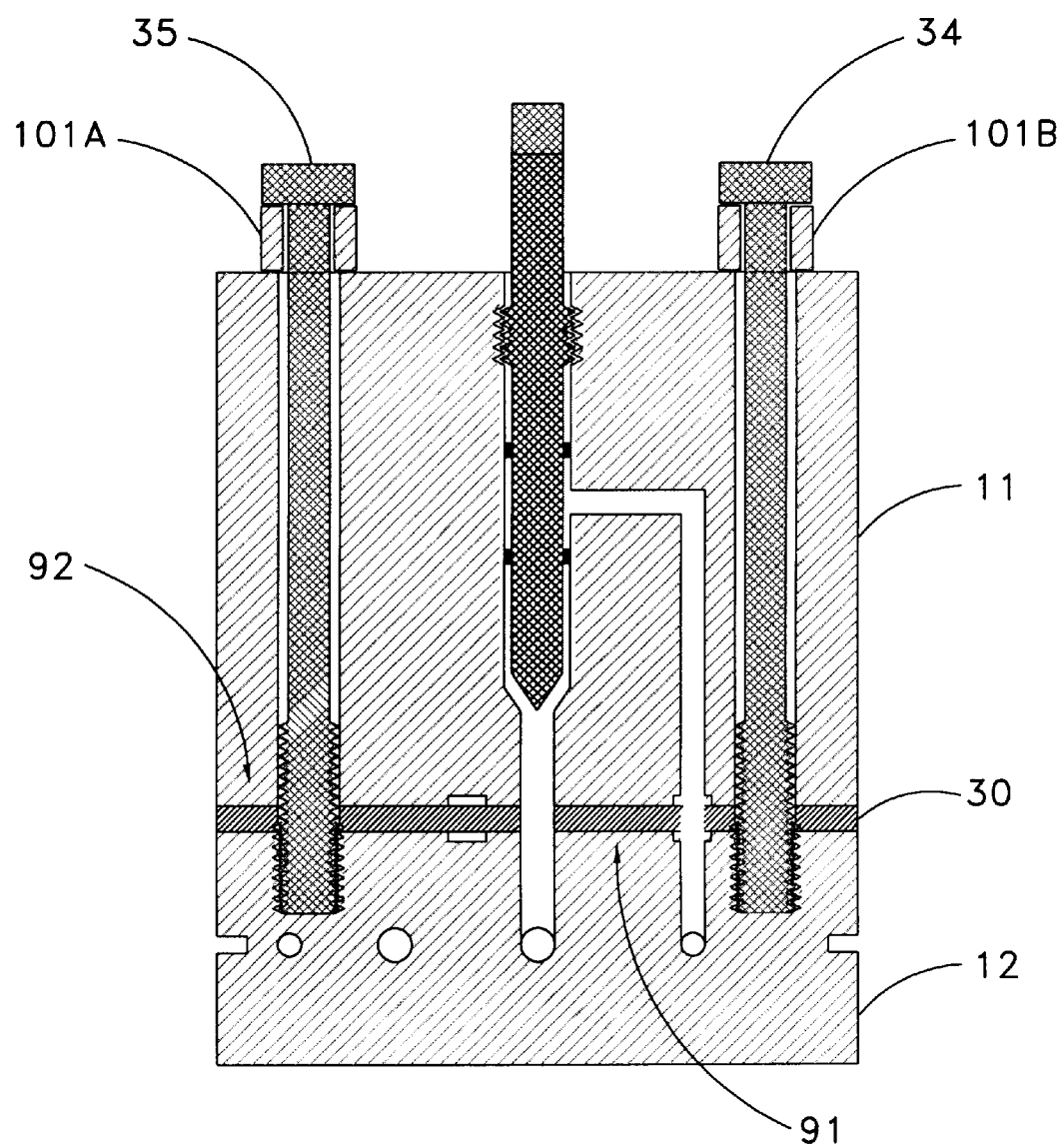
FIG. 12 sets forth a modification of FIG. 10 showing how bolt length can be increased by using spacers. Increasing bolt length increases the total bolt strain and its capability to compensate for fluid barrier displacement.

If the bolt length 34 and 35 required to traverse conditioning component module 11 is not sufficiently long to produce a strain equal to or greater than the thickness of fluid barrier material 30 than the bolt length can be increased by use of spacers 101A and 101B as shown in FIG. 12.

It has been determined that, as plastic displacement of fluid barrier material occurs thereby reducing bolt strain, the net clamping force required on opposite sides of fluid barrier material 30 to effect fluid sealing is diminished accordingly. This is probably due to filling of irregularities of surface 91 and 92 by fluid barrier material as previously mentioned.

It was found that when the fluid barrier material 30 thickness was 0.005 inches and the bolt 34 and 35 lengths were at least two inches long the first fluid barrier around the passage junctions were not breached by fluids at pressures in excess of 1000 pounds per square inch after extensive thermocycling from approximately 32° F. to 450° F.

Effect of Surface Geometry on Prevention of Fluid Barrier Breaching

Tests indicate that some of the major factors relating to fluid barrier blowout at high fluid pressures are the edge area of fluid barrier exposed to the fluid pressure, the plastic properties of the fluid barrier material 30, and the friction between he fluid barrier material 30 and the surfaces 91 and 92. With a given plastic material of construction of the fluid barrier material fluid pressure which causes fluid barrier blowout can be significantly increased by reducing the fluid barrier thickness in order to minimize its area exposed to fluid pressure.

Figure 13:
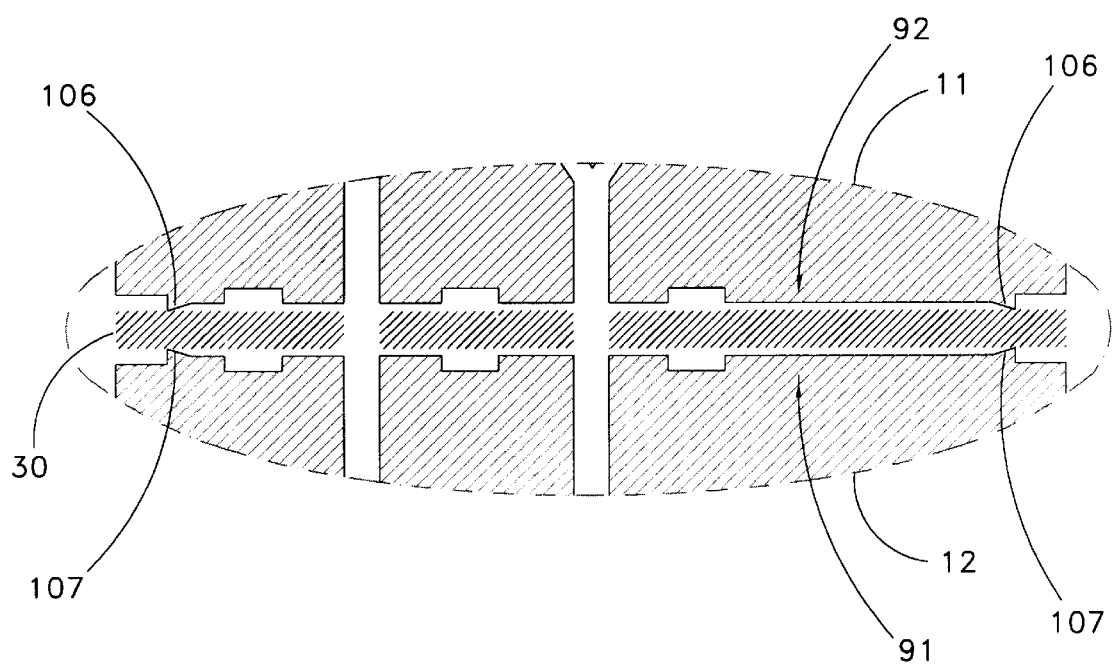
FIG. 13 is a modification of FIG. 11, showing a sloped segment in the surface depression in both modules for the purpose of forming a wedge fluid barrier. The modules surfaces are shown in contact with the fluid barrier material without a clamping force applied.
Figure 14:
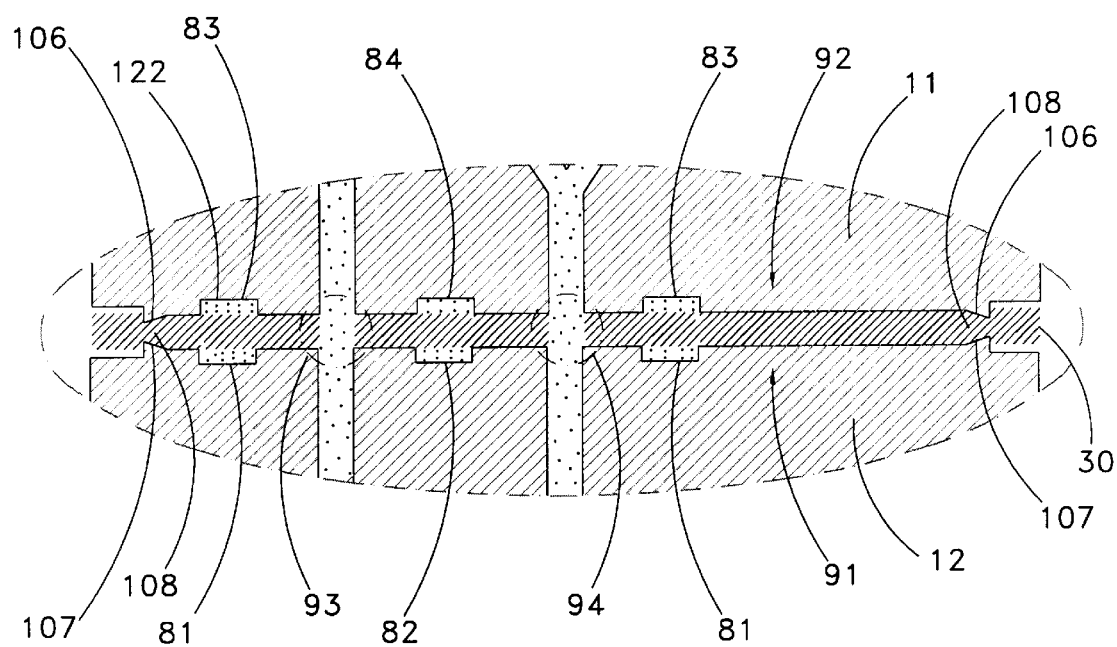
FIG. 14 further illustrates the invention of FIG. 13, after a clamping force has been applied causing the sloped surface segments to displace fluid barrier material thereby forming a wedge shaped fluid barrier which resists blowout.

Testing also revealed that for a given fluid barrier material the maximum leak-free operating pressure of internal fluids could be significantly extended by forming a slope on one or both sides in contact with he opposite sides of fluid barrier material. In FIG. 13 it can be seen that surface segment 106 of conditioning component module 11 and surface segment 107 of base module 12 are sloped. When a sufficient net clamping force (FIG. 14) is applied between conditioning component module 11 and base module 12 sloped surface 106 and 107 displace a portion of fluid barrier material 30, thereby creating a wedge shaped fluid barrier 108 sloped in opposition to the direction of the potential internal pressure applied by sample fluid 122 in passage grooves 81 and 83 and passage junctions 93 and 94 as shown in FIG. 14. The effect of increasing internal fluid pressure of sample fluid 122 is the wedging of fluid barrier 108. thereby creating a tighter seal. Fluid 122 may be present in passage grooves 81 and 83 in the event of a massive passage junction fluid barrier failure. The forming of a wedge shaped second fluid barrier is an additional measure of protection against sample fluid leaking to the environment.

Figure 15:
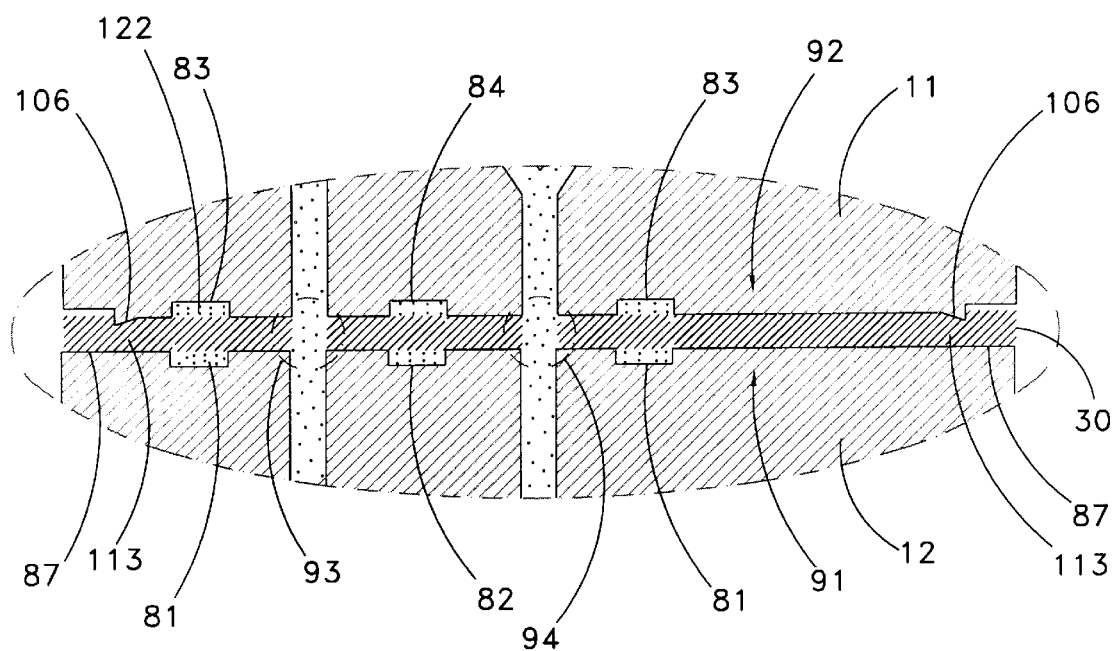
FIG. 15 provides a composite of FIG. 4A and FIG. 14, showing a sloped segment in the surface of the conditioning component module and a flat segment in the surface of the base module. This illustrates a half wedge shaped fluid barrier.

In FIG. 15, it can be seen that a single sloped surface 106 of conditioning component module 11 is used in conjunction with flat surface 87 of base module 12.

After sufficient clamping force has been applied between conditioning component module 11 and base module 12 to cause fluid barrier 30 to undergo plastic displacement, it can be seen that a ½ wedge shaped fluid barrier 113 was formed. The effect of increasing internal fluid pressure of sample fluid 122 in passage grooves 81 and 83 and passage junctions 93 and 94 is wedging of fluid barrier 113 thereby creating a tighter seal.

Figure 16:
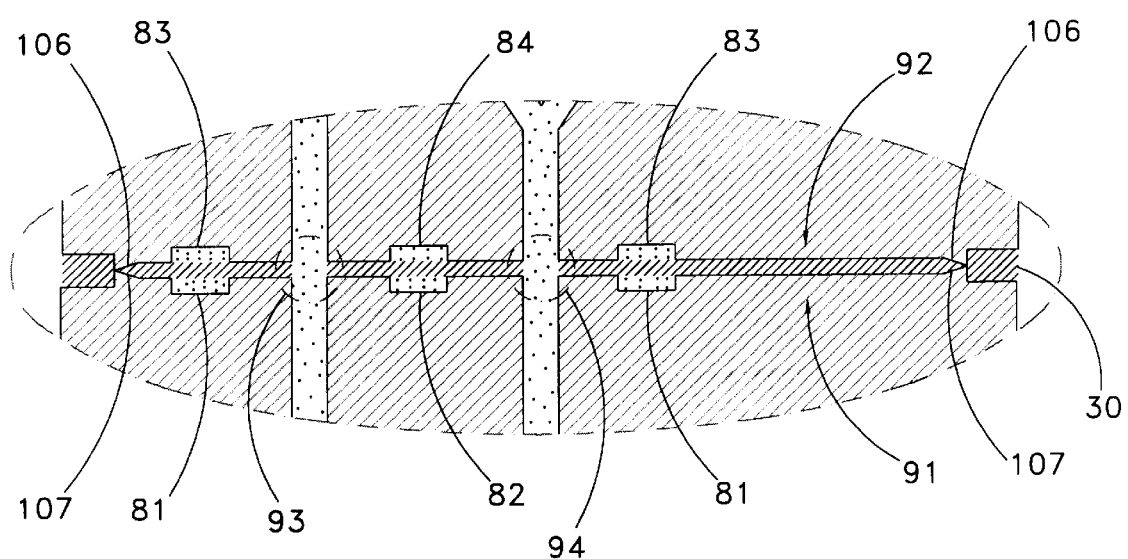
FIG. 16 sets forth the invention of FIG. 14, modified to show the sloped surfaces of both modules in contact as a result of applied clamping force, sloped surface depth, and fluid barrier thickness acting in concert.

In the preferred embodiment the depth of the sloped surfaces 106 and 107 is approximately 50% of the fluid barrier material 30 thickness and the fluid barrier material 30 thickness is less than 0.010 inches. In any case however, it is preferred that the depth of sloped surfaces 106 and 107; the depth of surfaces depressions 110 and 111; and he thickness of fluid barrier material 30 in combination, after sufficient clamping force has been applied between conditioning component module 11 and base module 12 to effect plastic displacement of fluid barrier 30, permit sloped surfaces 106 and 107 to make physical contact (FIG. 16). Depending on many factors such as the type and thickness of fluid barrier material 30, the initial clamping force between conditioning component module 11 and base module 12 may not result in plastic displacement until some period of time has elapsed.

Figure 17:
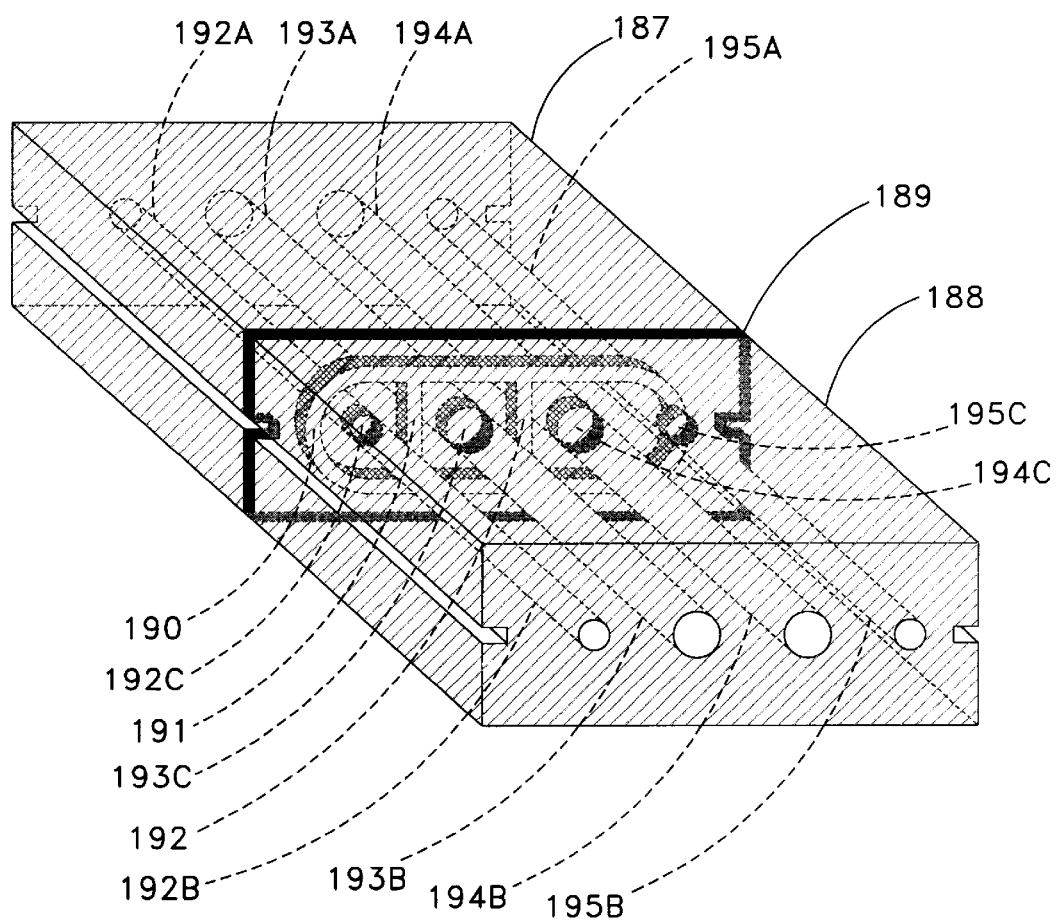
FIG. 17 provides an isometric view of two base module with fluid barrier inserted between showing only horizontal passages, and openings in the fluid barrier material. Vertical passages and conditioning component modules are not shown. This FIG. illustrates how adjacent base modules can be joined, and rendered leak free to the surrounding environment in a manner similar to the method utilized for achieving the same results with conditioning component modules and base modules.

The passage junctions between adjacent base module's in a Sample Conditioning System can be prevented from leaking fluid to the environment and to other passage junctions in a manner similar to that previously described by forming two fluid barriers and a leak containment passage around the passage junctions which are between a conditioning component module and base module. An example of this can be seen in FIG. 17 where passages 192A, 193A, 194A, and 195A of base module 187 form junctions with corresponding passages 192B, 193B, 194B, and 195B of base module 188 and opening 192C, 193C, 194C, and 195C of fluid barrier material 189. Collection grooves 190, 191, and 192 and passages 195A and 195B in concert, provide two series fluid barriers separated by a fluid collection passage in conformance with the invention and as previously detailed for conditioning component module 11 and base module 12. Therefore, hereinafter, when base modules are assembled side by side it must be assumed that the resulting passage junctions are rendered leak-free by the aforementioned methods.

Function and Attributes of Passages

In a manner similar to that in which corresponding vent collection passages 47, 70, 71, 72, 73, 74 and 75 of a plurality of base modules shown in FIG. 6 form a continuous passage 76 comprising a Sample Conditioning System fluid containment network as aforementioned, other continuous Sample Conditioning System passages can be formed for various purposes. As an example in FIG. 6 passages 114A, 114B, 115A, 115B, 116A, 116B, 117A, 117B, 118A, 118B, 119, and 123 comprise a passageway 124 in which sample fluid may flow through the desired component modules whereon sample conditioning occurs. Sample fluid in this example is conditioned in the manner required by the aforementioned first and second fluid circuits of the diagram of FIG. 3. A second example in FIG. 6 are passageways 125, 126, 127, 128, 129, 130A, 130B, and 131A, and 131B comprising passageway 132. In this example passages 130A, 130B, 131A, and 131B provide fluid communication among the component modules required by the aforementioned third fluid circuit of the diagram of FIG. 3. Passages 125, 126, 127, 128 and 129 serve as a conduit for sample fluid flow to an external destination not shown.

A third example is shown in FIG. 6 where corresponding passages of the assembled base module comprise a forth Sample Conditioning System passage 133 which in a preferred embodiment may function as a fluid transport passage for auxiliary fluids. Examples of auxiliary fluids which are anticipated for use in the Sample Conditioning System constructed by the methods of the invention are inert fluid for purging or cleaning the interior of the Sample Conditioning System and pressurized fluid for actuation of mechanical components such as automated valves.

Although not shown in FIG. 6, the passage junctions between adjacent base modules are sealed by the same method as previously described to seal passage junctions between conditioning component module 11 and base module 12, and between base modules 187 and 188, including the two fluid barriers with passage grooves formed in exterior surfaces for the purpose of collecting fluids which may breach the first fluid barrier of a passage junction.

Figure 18:
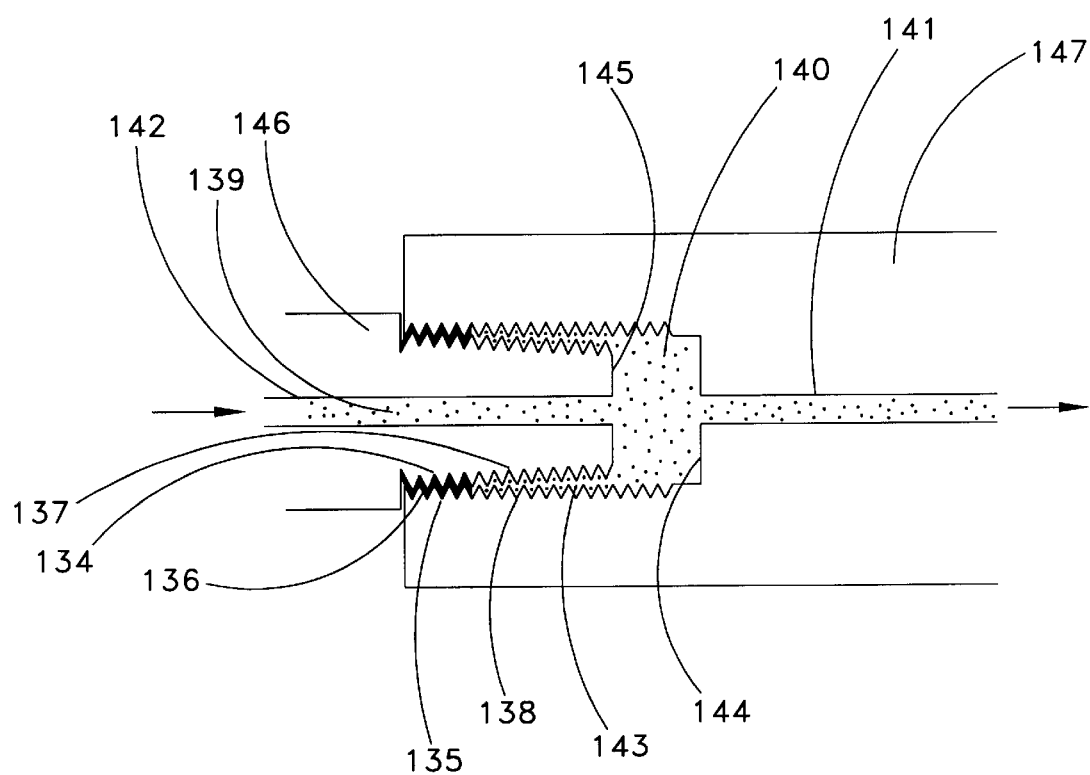
FIG. 18 is a cross sectional view of a typical male pipe threadingly engaged in a body containing female pipe threads. This view illustrates how cavities in this arrangement can trap fluids.
Figure 19:
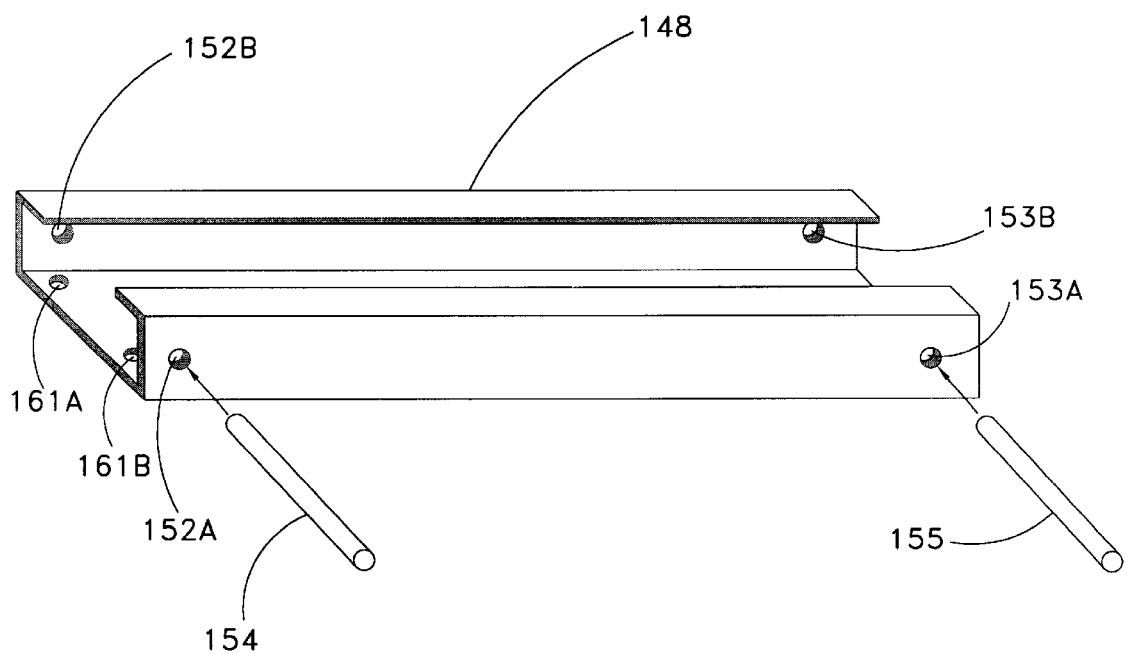
FIG. 19 provides an exploded isometric view of a mounting rail and pins.

Sample Conditioning System passages such as passages 76, 124, 132, and 133 seen in FIG. 6 formed and sealed in accordance with the methods of the invention are substantially better suited for transport of sample fluid within a Sample Conditioning System then the fluid transport passages of prior art. It can be seen in FIG. 18 that prior art use of pipe fittings in forming transport passages results in dead volume and tends to add to the overall Sample Conditioning System internal fluid volume. It can be seen that a segment of male threads 134, with the aid of fluid barrier material 136, form a fluid seal in combination with a segment of female threads 135. The cavity 143 between male thread segment 137 and female thread segment 138 is not in the direct path of sample fluid 139 flowing between passages 141 and 142. The cavity 140, formed between the leading surface 145 of male pipe fitting 146 and the bottom surface 144 of female pipe fittings 147, forms a reservoir for sample fluid 139.

The trapping or removing of sample fluids by cavities 140 and 143 from the direct sample fluid flow paths of passages 141 and 142 is highly undesirable. The effect of these type cavities on analytical results is well known in the art. The inventions method of forming, joining and sealing of sample fluid passages provide minimum volume passages absent static fluid pocket volume. An example of this is seen in FIG. 4 where passages 14 and 15 are joined at passage junction 93, the passage junction 93 performs a function similar to that of the aforementioned male pipe fittings 146 and female pipe fittings 147. Yet the interior of passage junction 93 does not contain dead or unpurged cavities such as cavity 143, nor does it have and enlarged volume such as cavity 140. Passage junction 93 provides near ideal characteristics for transporting sample fluids in a Sample Conditioning System.

Assembly and Mounting of Modules to Construct a Sample Conditioning System

The invention also includes a method for mounting of base modules, with attached conditioning component module's, that provides for proper alignment of corresponding passages in adjacent base modules, provides the clamping force between adjacent base module to form fluid barriers around passage junctions as aforementioned, and also provides a means for mounting an entire Sample Conditioning System constructed by the methods previously described.

Figure 20:
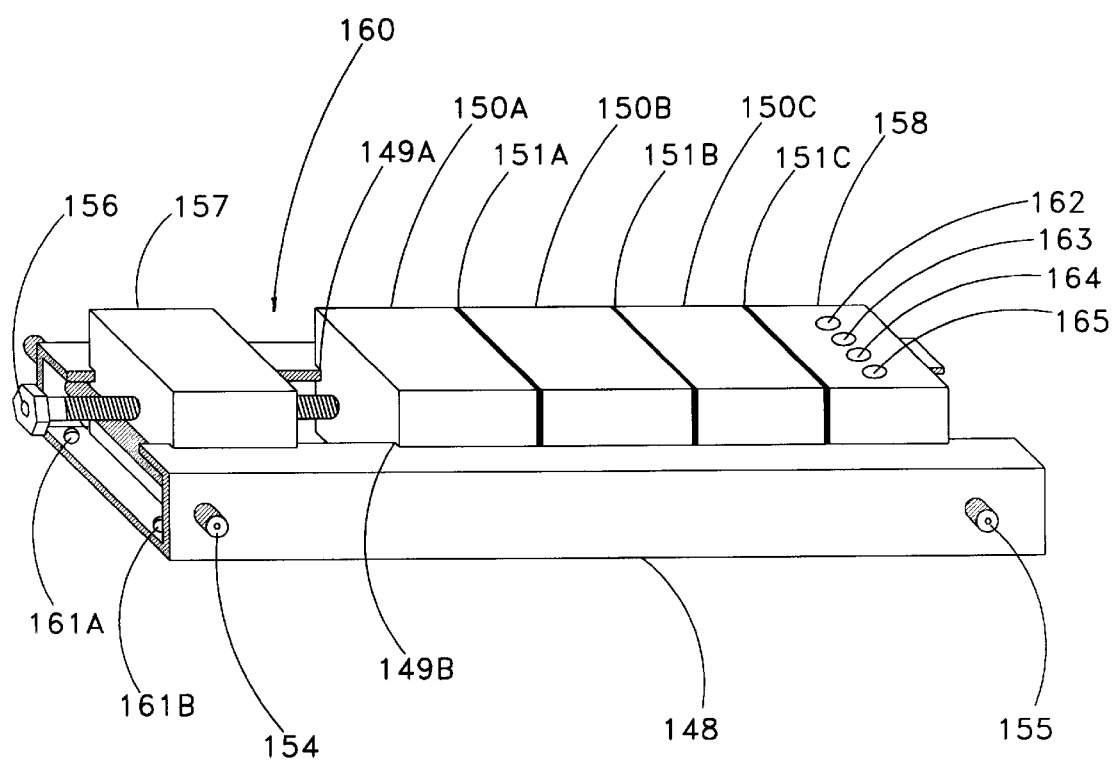
FIG. 20 illustrates an isometric, assembled view of three base modules and two termination modules on a mounting rail.
Figure 21:
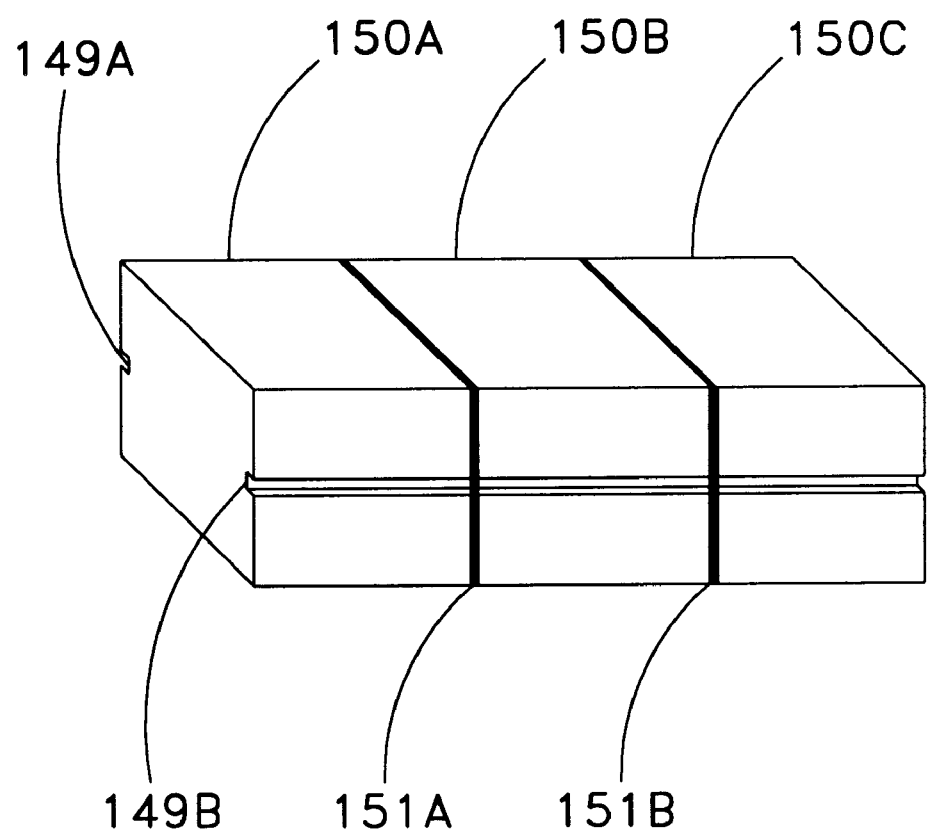
FIG. 21 sets forth an isometric view of the three base modules of FIG. 20 showing grooves in the modules which mate with the mounting rail.

The method consist of first constructing a mounting rail 148 as shown in FIG. 19, 20, 21, and 10. The mounting rail 148 slides into grooves 149A and 149B formed in the sides of base modules 150A, 150B, 150C, fluid barriers 151A, fluid barrier 151B, fluid barrier 151C, and termination modules 157 and 158 as shown in FIG. 20. For sake of clarity conditioning component module were not shown mounted on base modules 150A, 150B, and 150C. The mounting rail maintains alignment between adjacent modules and in conjunction with termination modules 157 and 158 provides a method for exerting a clamping force between base modules thereby compressing fluid barrier 151A, 151B, and 151C as required to effect sealing of base module and termination module passage junctions. A specific means for exerting the clamping force is shown in FIG. 20 although other means are known.

In this example a first termination module 158 is retained on mounting rail 148 by pin 155 inserted through holes 153A and 153B. A second termination module 157 is retained on mounting rail 148 by pin 154 inserted through holes 152A and 152B. A bolt 156 is threaded through termination module 157 with its end in contact with base module 150A. By tightening bolt 156 a clamping force is exerted which compresses fluid barriers 151A, 151B, and 151C as required to effect fluid sealing of base module and termination module passage junctions not shown, and secures the entire assembly which includes base modules 150A, 150B, and 150C fluid barriers 151A, 151B,and 151C termination modules 157 and 158 and pins 154 and 155. The assembly 160 can be mounted to a mounting surface 159 with screws 160A and 160B through holes 161A and 161B.

To remove a base module from the assembly 160, bolt 156 is loosened, pin 154 is removed, and base modules are slid from the mounting rail 148. Since the base modules do not perform any sample fluid conditioning functions they are not likely to require removal once in service. The conditioning component modules however can easily be removed and/or replaced from a Sample Conditioning System assembly by loosening and removing bolts 34 and 35 as seen in FIG. 10 and 12. It should be noted that passages not shown, formed in termination module 158 provide fluid communication between the base modules and external devices through openings such as openings 162, 163, 164, and 165 of FIG. 20 in a manner similar to that described for providing fluid communication between base module 12 and conditioning component module 11. In a manner similar to the method for imposing a strain in a threaded member for compensation of barrier material displacement, a strain can be imposed in the mounting rail 148, by tightening bolt 156, which will compensate for the collective displacement of all barrier material disposed between base modules mounted on the mounting rail.

Attachment for Fluid Transport Tube

The current invention also provides a means for attaching fluid transport tube to a device body such as a base module. Tubing attachments are necessary to conduct sample fluids between the Sample Conditioning System and external sample fluid sources or disposal sites. Prior art tubing attachments are a common and frequent source of fugitive emissions of sample fluids. The tubing attachment means of the current invention provides two fluid barriers in series with a collection passage. A collection passage serves to transport to an external disposal site fluids which may breach a first series fluid barrier.

A second fluid barrier prevents fluids in the collection passage from escaping to the surrounding environment. The function of the invention's tubing attachment and sealing method is similar to the two series fluid barriers with collection passage previously described for sealing passage junctions between conditioning component modules and base modules. Multiple series fluid barriers are well known in the prior art. Examples are the compression ferrules utilized by Swagelock®, Parker® Hannifin® and Tylok®. However, the prior art does not provide means for preventing leakage of sample fluid to the external environment by collecting and transporting to an external disposal site fluids which breach a first fluid barrier.

In the preferred embodiment (FIGS. 22A and 22B) a circular cavity 182 is formed in body segment 166. Body segment 166 represents a segment of the body of any fluid containment device. The diameter of cavity 182 is reduced in four successive steps resulting in the formation of circular ledges 171, 172, and 174, Fluid passage 170 is in fluid communication with cavity 182 between ledges 172 and 174. Female threads 176B are formed in the inner diameter of the cavity 182 between circular ledge 174 and outer surface 183. A nut 168 has male threads 176A formed on its lower end. When assembly 186 is assembled as shown, lower ferrule 173 rest upon ledge 172, upper ferrule 175 rests upon ledge 174, male threads 176A of nut 168 are threaded into female threads 176B of cavity 182; and tube 167 extends through the center holes of nut 168, upper ferrule 175, lower ferrule 173 and rests upon ledge 171. The center passage 177 of tube 167 is in approximate axial alignment with passage 169.

Upper ferrule 175 and lower ferrule 173 are rigidly attached and fluidly sealed to tube 167. Lower ferrule 173 and ledge 172 in combination form a first fluid barrier for sample fluid 184. Upper ferrule 175 and ledge 174 in combination form a second fluid barrier in series with the first fluid barrier. Cavity 178 and passage 170 in combination form a collection passage for sample fluid which may breach the first fluid barrier. Nut 168 forces contact between upper ferrule 175 and ledge 174 and between lower ferrule 173 and ledge 172 which in turn retains tube 167 in the position shown in assembled view FIG. 22B.

In normal service passages 170 and 169 provide fluid communication between body segment 166 and external fluid sources or fluid receiving sites not shown. Body segment 166 represents a segment of any device body which is utilized in the construction of a Sample Conditioning System. Should fluid contained in passages 169 and 177 breach the lower fluid barrier it enters cavity 178 then is transported by passage 170 to an external disposal site not shown. If body segment 166 is a segment of a conditioning component module, base module or termination module previously described, then passage 170 becomes an integral part of the Sample Conditioning System fluid containment network.

Another means of operating assembly 186 is to pressurize passage 170 with an inert gas to a pressure equal to or slightly in excess of the fluid pressure in passages 169 and 177. A failure of the lower fluid barrier would then result in inert gas from passage 170 flowing through cavity 178 and into passages 169 and 177 thereby preventing sample fluid contained in passages 169 and 177 from escaping to the surrounding atmosphere. Yet another means of operating assembly 186 is to evacuate passage 170 and cavity 178 by external vacuum means. In the event of a lower fluid barrier failure sample fluid entering cavity 178 will be conducted by passage 170 to an external disposal site not shown. Should the upper fluid barrier fail then fluids from the surrounding environment will enter cavity 178 and be transported by passage 170 to an external disposal site not shown. In any case, however, sample fluids cannot escape to the external atmosphere. The preferred embodiment described, assembly 186, achieves the desired two series fluid barriers separated by a fluid collection passage.

While certain specific embodiments and details have been described in order to illustrate the present invention, it will be apparent to those skilled in the art that many modifications can be made therein without departing from the basic concept and scope of the invention.

Further, the invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. A method for constructing a first fluid barrier, a fluid containment passage, and a second fluid barrier surrounding the junction of a first fluid passage terminating in a first surface and a second fluid passage terminating in a second surface, said method comprising the steps of:
   (a) forming a first groove in a first surface surrounding the termination of a first passage in said first surface, the inside perimeter of said first groove extending beyond the outside perimeter of said termination of the first passage in said first surface and the outside perimeter of said first surface extending beyond the outside perimeter of said first groove;
   (b) forming a second groove in a second surface surrounding the termination of a second passage in said second surface, the inside perimeter of said second groove extending beyond the outside perimeter of said termination of the passage in said second surface and the outside perimeter of said first surface extending beyond the outside perimeter of said second groove;
   (c) inserting a sheet of fluid barrier material between said first and second surfaces, said fluid barrier material having openings to permit fluid communication between passages terminating on the surfaces of said first surface and corresponding passages terminating on the surface of said second surface, the outside perimeter of said openings lying within the inside perimeter of said first and second grooves;
   (d) providing fluid communication between the said first groove and an external fluid disposal system;
   (e) providing fluid communication between the said second groove and an external fluid disposal system; and
   (f) compressing said sheet of fluid barrier material by forcing the first and second surfaces against opposing sides of said sheet of fluid barrier material.

2. The method of claim 1 where the thickness of the sheet of fluid barrier material is less than 0.040 inches.

3. The method of claim 2 where:
   (a) the force compressing the fluid barrier material is applied by one or more threaded members; and
   (b) the length of the threaded members and the force compressing the fluid barrier material result in a strain of a value equal to or exceeding the thickness of said fluid barrier material.

4. The method of claim 1 where the thickness of the sheet of fluid barrier material is less than 0.030 inches.

5. The method of claim 1 where the thickness of the sheet of fluid barrier material is less than 0.020 inches.

6. The method of claim 1 where the thickness of the sheet of fluid barrier material is less than 0.015 inches.

7. The method of claim 1 where the thickness of the sheet of fluid barrier material is less than 0.010 inches.

8. the method of claim 7 where;
   (a) the force compressing the sheet of fluid barrier material is applied by one or more threaded members and;
   (b) the length of the threaded and unthreaded members and the force compressing the sheet of fluid barrier material, result in a strain of a value equal to or exceeding the thickness of said sheet of fluid barrier material.

9. The method of claim 1 where the first and second surfaces are pressed against opposing surfaces of the sheet of fluid barrier material with a net force greater than 500 pounds per square inch of contact exclusive of the force exerted by internal fluid pressure.

10. The method of claim 9 wherein the net force is greater than 1000 pounds per square inch.

11. The method of claim 9 where the net force is greater than 1500 pounds per square inch.

12. The method of claim 9 where the net force is greater than 2000 pounds per square inch.

13. The method of claim 9 where the net force is greater than 2500 pounds per square inch.

14. The method of claim 9 where force applied to the first and second surfaces results in displacement of sheet fluid barrier material to a point where said first surface and second surface make contact.

15. The method of claim 9 where:
   (a) the force compressing the sheet of fluid barrier material is applied by one or more threaded members and;
   (b) the length of the threaded and unthreaded members and the force compressing the sheet of fluid barrier material, result in a strain of a value equal to or exceeding the thickness of said sheet of fluid barrier material.

16. The method of claim 1 where;
   (a) the force compressing the sheet of fluid barrier material is applied by one or more threaded members and;
   (b) the length of the threaded and unthreaded members and the force compressing the sheet of fluid barrier material, result in a strain of a value equal to or exceeding the thickness of said sheet of fluid barrier material.

17. The method of claim 16 where the thickness of the fluid barrier material is less than 0.040 inches.

18. The method of claim 16 where the thickness of the fluid barrier material is less than 0.030 inches.

19. The method of claim 16 where the thickness of the fluid barrier material is less than 0.020 inches.

20. The method of claim 16 where the thickness of the fluid barrier material is less than 0.015 inches.

21. The method of claim 16 where the thickness of the fluid barrier material is less than 0.010 inches.

22. The method of claim 16 where said first surface is sloped in opposition to the direction of applied fluid pressure.

23. The method of claim 16 where the said second surface is sloped in opposition to the direction of applied fluid pressure.

* * * * *